United States Patent
Herr et al.

(10) Patent No.: US 11,179,251 B2
(45) Date of Patent: Nov. 23, 2021

(54) METHOD AND SYSTEM FOR PROVIDING PROPRIOCEPTIVE FEEDBACK AND FUNCTIONALITY MITIGATING LIMB PATHOLOGY

(71) Applicant: Massachusetts Institute of Technology, Cambridge, MA (US)

(72) Inventors: Hugh M. Herr, Somerville, MA (US); Tyler Clites, Cambridge, MA (US); Benjamin Maimon, Brookline, MA (US); Anthony Zorzos, Cambridge, MA (US); Matthew J. Carty, Quincy, MA (US); Jean-Francois Duval, Malden, MA (US); Shriya Sruthi Srinivasan, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 235 days.

(21) Appl. No.: 16/068,531

(22) PCT Filed: Jan. 6, 2017

(86) PCT No.: PCT/US2017/012553
§ 371 (c)(1),
(2) Date: Jul. 6, 2018

(87) PCT Pub. No.: WO2017/120484
PCT Pub. Date: Jul. 13, 2017

(65) Prior Publication Data
US 2019/0021883 A1    Jan. 24, 2019

Related U.S. Application Data

(60) Provisional application No. 62/276,422, filed on Jan. 8, 2016.

(51) Int. Cl.
*A61F 2/72* (2006.01)
*A61N 1/36* (2006.01)
(Continued)

(52) U.S. Cl.
CPC .................. *A61F 2/72* (2013.01); *A61F 2/64* (2013.01); *A61F 2/80* (2013.01); *A61H 3/00* (2013.01);
(Continued)

(58) Field of Classification Search
CPC ...... A61F 2/72; A61F 2/64; A61F 2/80; A61F 2002/5059; A61F 2002/6827;
(Continued)

(56) References Cited

U.S. PATENT DOCUMENTS 3,735,425 A   5/1973   Hoshall et al.
4,492,233 A * 1/1985   Petrofsky ........... A61N 1/36003
                                                  128/905
(Continued)

FOREIGN PATENT DOCUMENTS

WO   1985005548 A1   12/1985
WO   2012/097297 A2   7/2012
(Continued)

OTHER PUBLICATIONS

Agnew et al., "Histologic and physiologic evaluation of electrically stimulated peripheral nerve: Considerations for the selection of parameters," Annals of Biomedical Engineering, vol. 17, pp. 39-60, 1989.
(Continued)

*Primary Examiner* — Yashita Sharma
*Assistant Examiner* — Melissa A Hoban
(74) *Attorney, Agent, or Firm* — Hamilton, Brook, Smith & Reynolds, P.C.

(57) ABSTRACT

Proprioceptive feedback is provided in a residual limb of a person that includes forming a linkage between a pair of
(Continued)

agonist and antagonist muscles, forming a sliding surface over which the agonist and antagonist muscles slide. The sliding surface can include a synovial sleeve, a bridge formed between the distal ends of bones, or a fixture that is osseointegrated into the bone. The invention also includes a system for transdermal electrical communication in a person that includes a percutaneous access device, a sensory device that communicates signals between a muscle and the percutaneous device, and a stimulation device in communication with the percutaneous access device. In another embodiment, a closed-loop functional stimulation system restores lost functionality to a person that suffers from impairment of a neurological control system or at least partial loss of a limb.

11 Claims, 24 Drawing Sheets

(51) Int. Cl.

| | | |
|---|---|---|
| *A61F 2/64* | (2006.01) | |
| *A61F 2/80* | (2006.01) | |
| *A61H 3/00* | (2006.01) | |
| *A61N 5/06* | (2006.01) | |
| A61F 2/78 | (2006.01) | |
| A61N 1/05 | (2006.01) | |
| A61F 2/50 | (2006.01) | |
| A61F 2/68 | (2006.01) | |
| A61F 2/70 | (2006.01) | |

(52) U.S. Cl.
CPC ....... *A61N 1/36003* (2013.01); *A61N 5/0622* (2013.01); *A61F 2002/5059* (2013.01); *A61F 2002/6827* (2013.01); *A61F 2002/6872* (2013.01); *A61F 2002/6881* (2013.01); *A61F 2002/704* (2013.01); *A61F 2002/705* (2013.01); *A61F 2002/7887* (2013.01); *A61H 2201/5058* (2013.01); *A61N 1/0551* (2013.01); *A61N 1/36017* (2013.01)

(58) Field of Classification Search
CPC ...... A61F 2002/6872; A61F 2002/6881; A61F 2002/704; A61F 2002/705; A61F 2002/7887; A61H 3/00; A61H 2201/5058; A61N 5/0622; A61N 1/36003; A61N 1/36017; A61N 1/0551
See application file for complete search history.

(56) References Cited

U.S. PATENT DOCUMENTS

| | | | |
|---|---|---|---|
| 4,750,499 | A | 6/1988 | Hoffer |
| 5,158,097 | A | 10/1992 | Christlieb |
| 5,674,262 | A * | 10/1997 | Tumey ................. A61H 9/0078 607/48 |
| 5,769,875 | A * | 6/1998 | Peckham ........... A61N 1/36003 607/116 |
| 5,824,027 | A | 10/1998 | Hoffer et al. |
| 6,456,866 | B1 | 9/2002 | Tyler et al. |
| 7,260,436 | B2 | 8/2007 | Kilgore et al. |
| 7,367,958 | B2 | 5/2008 | McBean et al. |
| 7,396,337 | B2 | 7/2008 | McBean et al. |
| 7,725,175 | B2 | 5/2010 | Koeneman et al. |
| 9,352,146 | B2 | 5/2016 | Langhals et al. |
| 9,474,634 | B2 | 10/2016 | Herr et al. |
| 10,213,324 | B2 * | 2/2019 | Lenzi ..................... A61F 2/70 |
| 10,376,389 | B2 | 8/2019 | Gaston et al. |
| 2003/0144710 | A1 | 7/2003 | Haugland et al. |
| 2004/0106881 | A1 | 6/2004 | McBean et al. |
| 2004/0111130 | A1 | 6/2004 | Hrdlicka et al. |
| 2006/0224203 | A1 | 10/2006 | Hettrick et al. |
| 2007/0038311 | A1 | 2/2007 | Kuiken et al. |
| 2007/0191743 | A1 | 8/2007 | McBean et al. |
| 2008/0139968 | A1 | 6/2008 | Endo et al. |
| 2008/0228240 | A1 | 9/2008 | Edell et al. |
| 2008/0234781 | A1 | 9/2008 | Einav et al. |
| 2008/0243216 | A1 | 10/2008 | Zilberman et al. |
| 2009/0221896 | A1 | 9/2009 | Rickert et al. |
| 2009/0292325 | A1 | 11/2009 | Cederna et al. |
| 2010/0324699 | A1 * | 12/2010 | Herr ..................... B25J 9/1075 623/27 |
| 2011/0046506 | A1 * | 2/2011 | Durand ................. G06F 30/20 600/547 |
| 2011/0257501 | A1 | 10/2011 | Huys et al. |
| 2013/0253606 | A1 | 9/2013 | Youn et al. |
| 2013/0304174 | A1 | 11/2013 | Langhals et al. |
| 2014/0005763 | A1 | 1/2014 | Cederna et al. |
| 2014/0058495 | A1 | 2/2014 | Sakai et al. |
| 2014/0067083 | A1 | 3/2014 | Wenstrand et al. |
| 2015/0173918 | A1 | 6/2015 | Herr et al. |
| 2016/0051383 | A1 | 2/2016 | Goldfarb et al. |
| 2016/0074180 | A1 * | 3/2016 | Lenzi ....................... A61F 2/60 623/24 |
| 2016/0346099 | A1 | 12/2016 | Herr et al. |

FOREIGN PATENT DOCUMENTS

| | | |
|---|---|---|
| WO | 2013150298 A1 | 10/2013 |
| WO | 2015/061453 A1 | 4/2015 |

OTHER PUBLICATIONS

Aitken, "The effect of peripheral connexions on the maturation of regenerating nerve fibres", Journal of Anatomy, vol. 83, No. 1, pp. 32-43, 1949.
Akin, T., et al., "A Micromachined Silicon Sieve Electrode for Nerve Regeneration Applications," IEEE Transactions on Biomedical Engineering, 41(4): 305-313 (1994).
Au, S. K., et al., "Powered Ankle-Foot Prosthesis Improves Walking Metabolic Economy," IEEE Transactions on Robotics, 25(1): 51-66 (2009).
Biewener, Biomechanics: Structures and Systems, Oxford Univ. Press, Oxford, New York, Tokyo, Title Page and Table of Contents, (1992).
Bradley et al., "Functional regeneration of glossopharyngeal nerve through micromachined sieve electrode arrays," Brain Research, vol. 594, No. 1, pp. 84-90, 1992.
Bradley et al., "Long term chronic recordings from peripheral sensory fibers using a sieve electrode array," Journal of Neuroscience Methods, vol. 73, No. 2, pp. 177-186, 1997.
Branner et al., "A multielectrode array for intrafascicular recording and stimulation in sciatic nerve of cats," Brain Research Bulletin, vol. 51, No. 4, pp. 293-306, 2000.
Cravioto et al., "Clinical and ultrastructural study of painful neuroma", Neurosurgery, vol. 8, No. 2, pp. 181-190, 1981.
De Luca, C. J., "Surface Electromyography: Detection and Recording," DelSys Incorporated, (2002).
Dellon et al., "Treatment of the painful neuroma by neuroma resection and muscle implantation", Plastic and Reconstructive Surgery, vol. 77, No. 3, pp. 427-438, 1986.
Edell et al., "Bi-directional peripheral nerve interface for the control of powered prosthetic limbs," DARPA Contract N6600 1-05-C-8030, 2006.
Edell, "A peripheral nerve information transducer for amputees: long-term multichannel recordings from rabbit peripheral nerves," IEEE Transactions on Biomedical Engineering, vol. 33, No. 2,pp. 203-214, 1986.
Edin et al., "Finger movement responses of cutaneous mechanoreceptors in the dorsal skin of the human hand," Journal of Neurophysiology, vol. 65, pp. 657-670, 1991.
Farnsworth, "Wireless Implantable EMG Sensing Microsystem." Master's thesis, Case Western Reserve University (2010).

(56) References Cited

OTHER PUBLICATIONS

Fitzgerald et al., "Microchannels as axonal amplifiers," IEEE Transactions on Biomedical Engineering, vol. 55, No. 3, pp. 1136-1146, 2008.
Fitzgerald et al., "A regenerative microchannel neural interface for recording from and stimulating peripheral axons in vivo," Journal of Neural Engineering, vol. 9, No. 1, pp. 1-13, 2012.
Gaston et al. "A novel muscle transfer for independent digital control of a myoelectric prosthesis: the starfish procedure". Journal of Hand Surgery Am. Apr. 3, 2018. (Year: 2018).
Grandjean et al., "Recruitment properties of monopolar and bipolar epimysial electrodes," Annals of Biomedical Engineering, vol. 14, No. 1, pp. 53-66, 1986.
Haugland et al, "Restoration of lateral hand grasp using natural sensors," Artificial Organs, vol. 21, No. 3, pp. 250-253, 1997.
Herr et al., "Bionic ankle-foot prosthesis normalizes walking gait for persons with leg amputation," Proc. R. Soc. B, 279(1728): 457-464 (2012).
Jezernik et al., "Detection and inhibition of hypelTeflexia-like bladder contractions in the cat by sacral nerve root recording and electrical stimulation," Neurourology and Urodynamics, vol. 20, No. 2, pp. 215-230, 2001.
Kim et al., "Materials for multifunctional balloon catheters with capabilities in cardiac electrophysiological mapping and ablation therapy," Nature Materials, vol. 10, pp. 316-323, 2011.
Kovacs et al., "Regeneration microelectrode array for peripheral nerve recording and stimulation," IEEE Transactions on Biomedical Engineering, vol. 39,No. 9,pp. 893-902, 1992.
Kuiken et al., "The effect of subcutaneous fat on myoelectric signal amplitude and cross-talk," Prosthetics and Orthotics International, 27(1): 48-54 (2003).
Kuiken et al., "Targeted Muscle Reinnervation for Real-time Myoelectric Control of Multifunction Artificial Arms," JAMA, 301 (6): 619-628 (2009).
Kuiken, "Targeted reinnervation for improved prosthetic function," Physical Afedicine and Rehabilitation Clinics of North America, vol. 17, No. 1, pp. 1-13, 2006.
Lacour et al., "Long micro-channel electrode arrays: a novel type of regenerative peripheral nerve interface," IEEE Transactions on Neural Systems and Rehabilitation Engineering, vol. 17, No. 5, pp. 454-460, 2009.
Larson et al., "Prototype sensory regenerative peripheral nerve interface for artificial limb somatosensory feedback," Plastic & Reconstructive Surgery, vol. 133, No. 3S,pp. 26-27,2014.
Lawrence et al., "Long-term biocompatibility of implanted polymer-based intrafascicular electrodes," Journal of Biomedical Materials Research, vol. 63, No. 5, pp. 501-506, 2002.
Malagodi et al., "An intrafascicular electrode for recording of action potentials in peripheral nerves," Annals of Biomedical Engineering, vol. 17, pp. 397-410, 1989.
Martinez-Villalpando et al., "Agonist-antagonist active knee prosthesis: A preliminary study in level-ground walking," Journal of Rehabilitation Research & Development, 46(3): 361-374 (2009).
Martini, R., et al., "The L2/HNK-1 Carbohydrate Is Preferentially Expressed by Previously Motor Axon-associated Schwann Cells in Reinnervated Peripheral Nerves," The Journal of Neuroscience, 14(11): 7180-7191 (1994).
Naples et al., "A spiral nerve cuff electrode for peripheral nerve stimulation," IEEE Transactions on Biomedical Engineering, vol. 35, No. 11, pp. 905-916, 1988.
Navarro et al., "Stimulation and recording from regenerated peripheral nerves through polyimide sieve electrodes," Journal of the Peripheral Nervous System, vol. 3, No. 2, pp. 91-101, 1998.
Ochoa et al.., "Sensations Evoked by Intraneural Microstimulation of Single Mechanoreceptor Units Innervating the Human Hand," J. Physiol., 342: 633-654 (1983).
Okuda, T., et al., "The Autotomy Relief Effect of a Silicone Tube Covering the Proximal Nerve Stump," J. Orthop. Res., 24(7): 1427-1437 (2006).
Roll et al., "Kinesthetic role of muscle afferents in man, studied by tendon vibration and microneurography," Experimental Brain Research, vol. 4 7, No. 2, pp. 177-190, 1982.
Rouse et al., "Clutchable Series-Elastic Actuator: Design of a Robotic Knee Prosthesis for Minimum Energy Consumption," Proceedings of the IEEE International Conference on Rehabilitation Robotics (2013).
Schuettler et al., "18polar hybrid cuff electrodes for stimulation of peripheral nerves," in Proceedings of the International Functional Electrical Stimulation Society, Aalborg, Denmark, pp. 265-268, 2000.
Sosa et al., "Immunosuppressants: Neuroprotection and promoting neurological recovery following peripheral nerve and spinal cord lesions," Experimental Neurology, vol. 195, pp. 7-15, 2005.
Tian et al., "Macroporous nanowire nanoelectronic scaffolds for synthetic tissues," Nature Materials, vol. 11, pp. 986-994, 2012.
Vallbo, "Basic patterns of muscle spindle discharges in man," in Muscle Receptors and Movement, A. Taylor and A. Prochazka, Eds. London: Macmillan, 1981, pp. 263-275.
Veraart et al., "Selective control of muscle activation with a multipolar nerve cuff electrode," IEEE Transactions on Biomedical Engineering, vol. 40, No. 7, pp. 640-653, 1993.
Vrbova et al., "Chemical communication between regenerating motor axons and Schwann cells in the growth pathway," European Journal of Neuroscience, vol. 30, No. 3, pp. 366-375, 2009.
Wallman et al., "The geometric design of micromachined silicon sieve electrodes influences functional nerve regeneration," Biomaterials, vol. 22, No. 10, pp. 1187-1193, 2001.
Wallman et al., "Perforated silicon nerve chips with doped registration electrodes: in vitro performance and in vivo operation," IEEE Transactions on Biomedical Engineering, vol. 46, No. 9, pp. 1065-1073, 1999.
Walmsley et al., "Forces Produced by Medical Gastrocnemius and Soleus Muscles During Locomotionin Freely Moving Cats," J. Neurophysiol. vol. 41, No. 5, (1978), pp. 1203-1216.
Weir et al., "Implantable Myoelectric Sensors (IMESs) for Intramuscular Electromyogram Recording," IEEE Transactions on Biomedical Engineering, 56(1): 159-171 (2009).
Yoshida et al., "Peripheral nerve recording electrodes and techniques," in Neuroprostheses in Theory and Practice vol. 2, K. W. Horeb and G. S. Dhillon, Eds. Hakensack, NJ: World Scientific, 2004, pp. 683-744.
Dodson et al. "Case study: surgical prosthetic and therapeutic considerations for a patient with ipsilateral brachial plexus injury and transradial amputation," MyoElectric Controls/Powered Prosthetics Symposium, Fredericton, New Brunswick, Canada, Aug. 14, 2011.
Stevanovic et al. "Functional Free muscle transfer for upper extremity reconstruction," Plastic Reconstructive Surgery 134: 257e, Aug. 2014.
Hijawi et al. "Improved myoelectric prosthesis control accomplished using multiple nerve transfers," Plastic Reconstructive Surgery 118: 1573. 2006.
Gaston et al. "A novel muscle transfer for independent digital control of a myoelectric prosthesis: the starfish procedure," Journal of Hand Surgery Am. Apr. 3, 2018.
Venkatramani et al. "Role of free functioning muscle transfer in improving the functional outcomes following replantation of crush avulsion amputations of the forearm," Department of Plastic, Hand and Reconstructive Microsurgery, Ganga Hospital, Coimbatore, India. S105-S110, 2019.
Kuiken et al. "Targeted reinnervation for enhanced prosthetic arm function in a woman with a proximal amputation: a case study," The Lancet. vol. 369 pp. 371-380, Feb. 3, 2007.
Dumanian et al. "Targeted reinnervation for transhumeral amputees: current surgical technique and update on results," Plastic Reconstructive Surgery 124: 863, 2009.
Kuiken et al. "the use of target muscle reinnervation for improved myoelectric prosthesis control in a bilateral shoulder disarticulation amputee," Prosthetics and Orthotics International, 28, pp. 245-253, 2004.

(56) References Cited

OTHER PUBLICATIONS

Yoshida et al., "Characterization of signals and noise rejection with bipolar longitudinal intrafascicular electrodes," IEEE Transactions on Biomedical Engineering, vol. 46, No. 2, pp. 226-234, 1999.
Herr "The new bionics that let us run, climb and dance", TED 2014; Filmed Mar. 2014; Available at https://www.ted.com/talks/hugh_herr_the_new_bionics_that_let_us_run_climb_and_dance (Retrieved from the Internet on Apr. 15, 2015).
International Search Report and Written Opinion for Int'l Application No. PCT/US2017/012553, titled: Method and System for Providing Proprioceptive Feedback and Functionality Mitigating Limb Pathology, dated Jun. 16, 2017.
International Preliminary Report on Patentability for Int'l Application No. PCT/US2017/012553, titled: Method and System for Providing Proprioceptive Feedback and Functionality Mitigating Limb Pathology, dated Jul. 10, 2018.
Brindley, G. S., et al., "Sacral anterior root stimulators for bladder control in paraplegia: the first 50 cases," Journal of Neurology, Neurosurgery, & Psychiatry, 49(10): 1104-14 (1986).
"New device gives heart failure patients more freedom," UChicago Medicine, Oct. 30, 2000, 6 pages.
Forrest, G. P., et al., "Use of the Case Western Reserve/Veterans Administration neuroprosthesis for exercise, standing and transfers by a paraplegic subject," Disability and Rehabilitation Assistive Technology, 7(4): 340-344 (2012).
Frost, C. M., et al., "Neuroprosthetic hand real-time proportional control by rodent regenerative peripheral nerve interfaces," Plastic & Reconstructive Surgery, 133(4S): 1012-3 (2014).
Haugland, M. and T. Sinkjaer, "Cutaneous whole nerve recordings used for correction of foot drop in hemiplegic man," IEEE Transactions on Biomedical Engineering, 3(4): 307-317 (1995).
Hoffer, J. A., et al., "Roles of muscle activity and load on the relationship between muscle spindle length and whole muscle length in the freely walking cat," Prog. Brain Res., 80: 75 (1989).
Hulliger, M., "The mammalian muscle spindle and its central control," Reviews of Physiology, Biochemistry and Phamacology, 101: 1-110 (1984).
Jackson, B. M., et al., "Extension of borderzone myocardium in postinfarction dilated cardiomyopathy," Journal of the American College of Cardiology, 40(6): 1160-7; discussion 1168-71 (2002).
Kantrowitz A., et al. Development of a percutaneous energy transmission system, annual report prepared for Devices and Technology Branch, Division of Heart and Vascular Diseases, Natl Heart Lung and Blood Institute: Apr. 16, 1979. 70 pages.
Krishnaswamy, P., et al., "Human leg model predicts ankle muscle-tendon morphology, state, roles and energetics in walking," PLoS Computational Biology, 7(3): e1001107 (2011). http://doi.org/10.1371/journal.pcbi.1001107.
Leevering, K., P950035. Premarket Approval of NeuroControl Corporation Freehand System. CDRH (Aug. 15, 1997).
Loeb, G.E., "Cochlear prosthetics," Annual Review of Neuroscience, 13: 357-371 (1990).

Markowitz, J. (2013). A Data-Driven Neuromuscular Model of Walking and its Application to Prosthesis Control by. Massachusetts Institute of Technology.
Ortiz-Catalan, M., et al., "On the viability of implantable electrodes for the natural control of artificial limbs: review and discussion," Biomedical Engineering Online, 11: 33 (2012). http://doi.org/10.1186/1475-925X-11-33.
Kantrowitz A., et al. Development of a percutaneous energy transmission system, annual report prepared for Devices and Technology Branch, Division of Heart and Vascular Diseases, Natl Heart Lung and Blood Institute: Apr. 16, 1980. 77 pages.
Peckham, P.H. and J.S. Knutson, "Functional electrical stimulation for neuromuscular applications," Annu Rev Biomed Eng, 7: 327-60 (2005).
Ribot-Ciscar, E., and J. P. Roll, "Ago-antagonist muscle spindle inputs contribute together to joint movement coding in man," Brain Research, 791(1-2), 167-176 (1998).
Riso, R. R., et al., "Nerve cuff recordings of muscle afferent activity from tibial and peroneal nerves in rabbit during passive ankle motion," IEEE Transactions on Rehabilitation Engineering, 8(2): 244-258 (2000).
Roberts, T. J., et al., "Muscular force in running turkeys: the economy of minimizing work," Science, 275(5303): 1113-1115 (1997).
Sahin, M., et al., "Chronic recordings of hypoglossal nerve activity in a dog model of upper airway obstruction," Journal of Applied Physiology, 87(6): 2197-2206 (1999).
Tan, D. W., et al., "A neural interface provides long-term stable natural touch perception," Science Translational Medicine, 6(257): 257ra138-257ra138 (2014). http://doi.org/10.1126/scitranslmed.3008669.
Taylor, P., et al., "The functional impact of the Freehand System on tetraplegic hand function," Clinical Results. Spinal Cord, 40(11): 560-6 (2002).
Urbanchek, M. G., et al., "Regenerative peripheral nerve interface function at 1 and 3 months after implantation," Plastic & Reconstructive Surgery, 130(1S): 84 (2012).
Veraart, C., et al., "Pattern recognition with the optic nerve visual prosthesis," Artificial Organs, 27(11): 996-1004 (2003).
Vrbová, G., Application of muscle/nerve stimulation in health and disease. Advances in muscle research. 2008, New York: Springer. xi, p. 118.
Kantrowitz A., et al. Development of a percutaneous energy transmission system, annual report prepared for Devices and Technology Branch, Division of Heart and Vascular Diseases, Natl Heart Lung and Blood Institute: Oct. 9, 1981. 70 pages.
Kantrowitz A., et al. Development of a percutaneous energy transmission system, annual report prepared for Devices and Technology Branch, Division of Heart and Vascular Diseases, Natl Heart Lung and Blood Institute: May 27, 1982. 47 pages.
Kantrowitz A., et al. Development of a percutaneous energy transmission system, annual report prepared for Devices and Technology Branch, Division of Heart and Vascular Diseases, Natl Heart Lung and Blood Institute: Jun. 5, 1983. 76 pages.

* cited by examiner

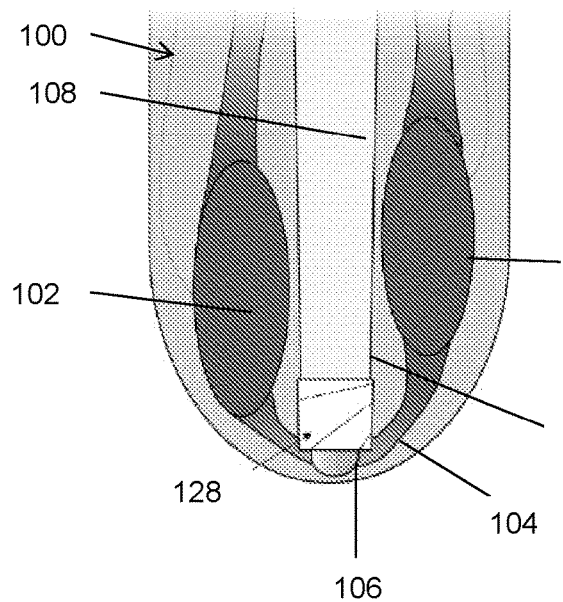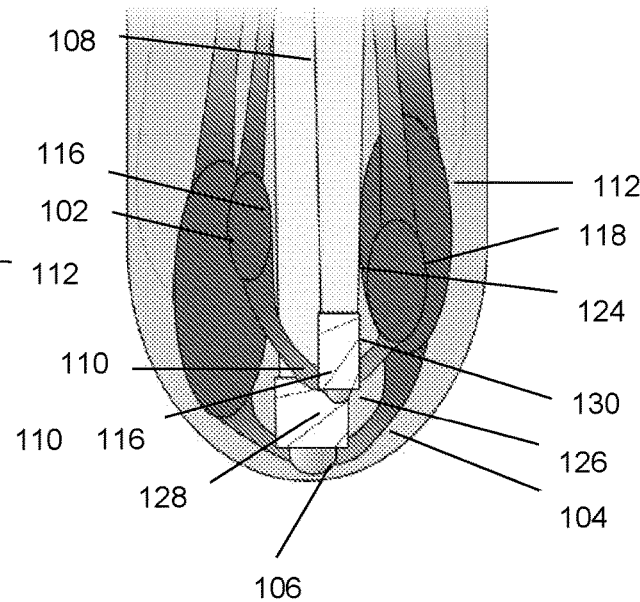

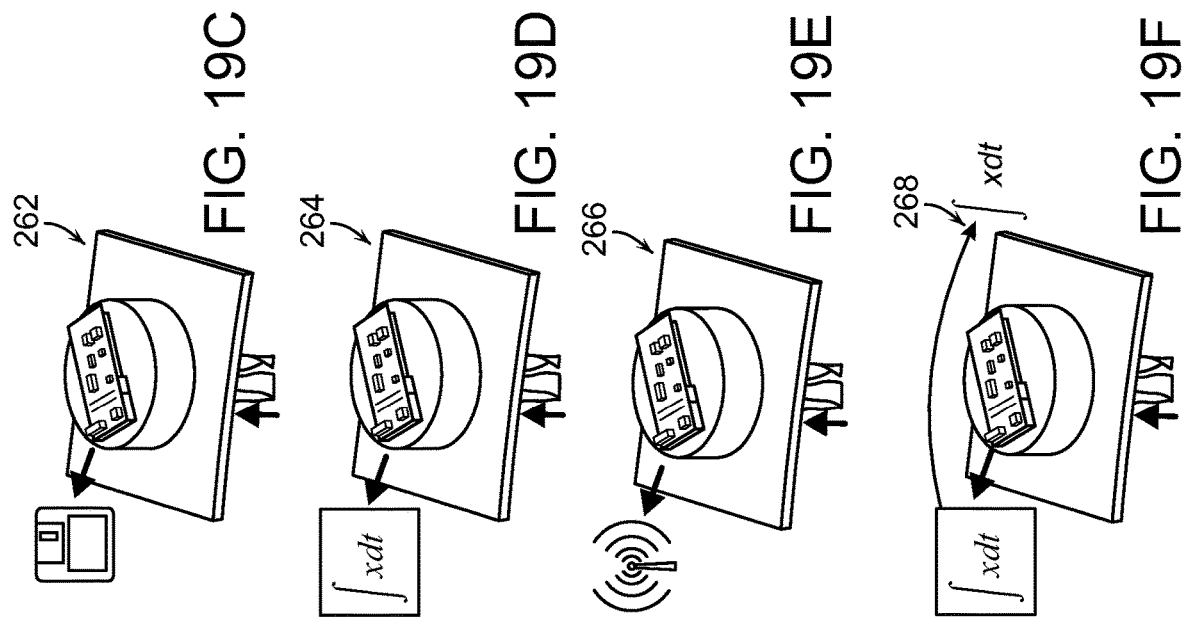
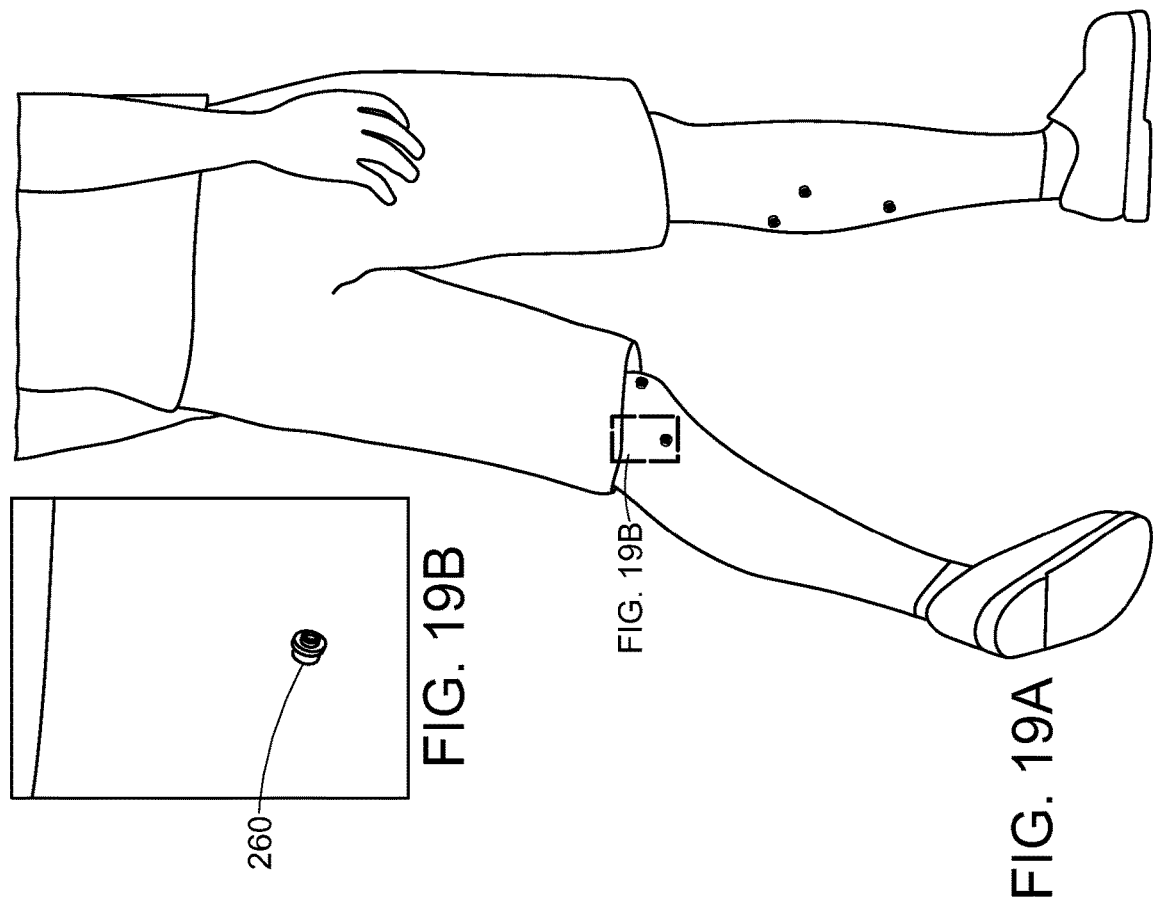

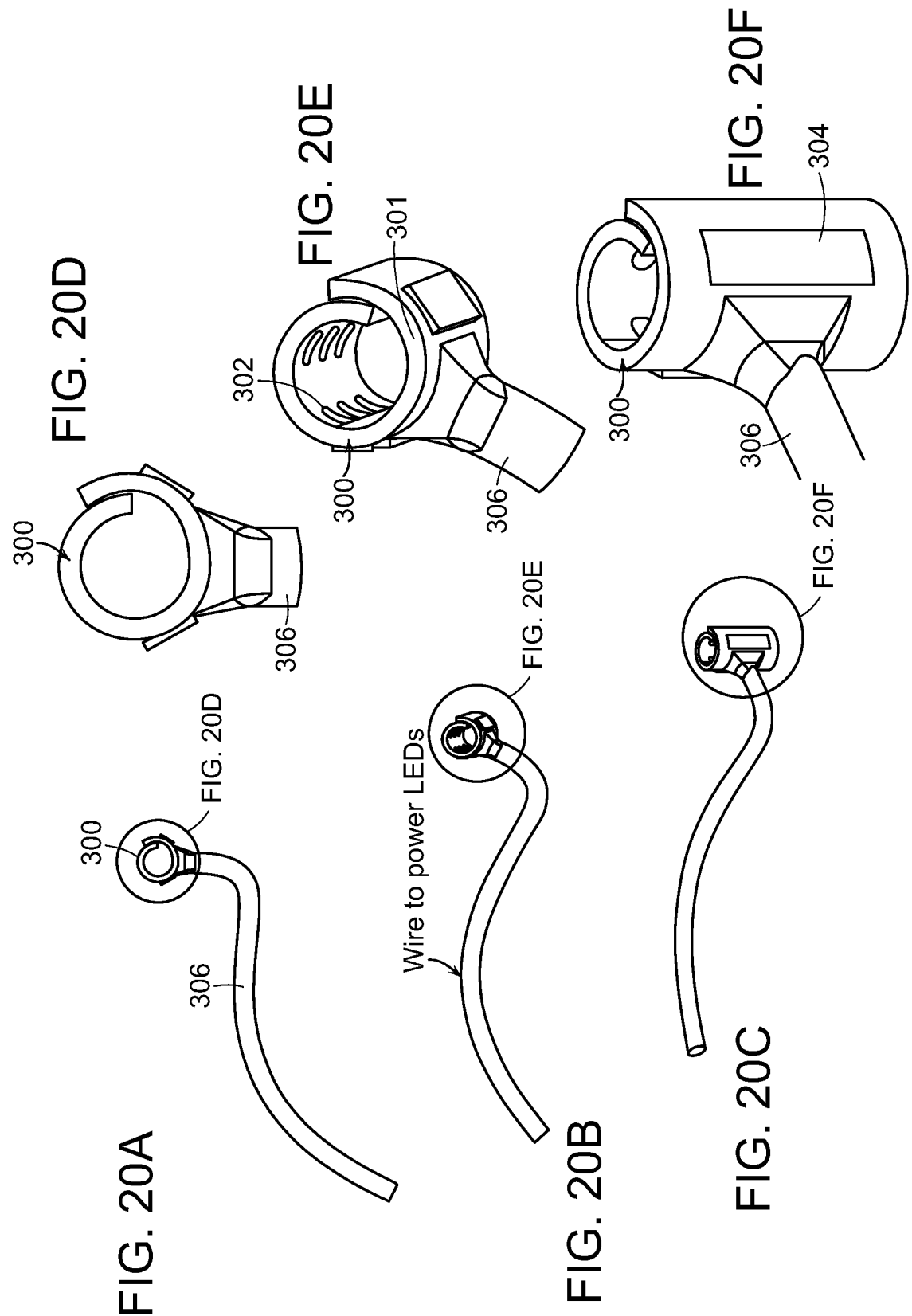

Optical Stimulation v0.1

Sonomicrometer v0.2

METHOD AND SYSTEM FOR PROVIDING PROPRIOCEPTIVE FEEDBACK AND FUNCTIONALITY MITIGATING LIMB PATHOLOGY

RELATED APPLICATION

This application is the U.S. National Stage of International Application No. PCT/US2017/012553, filed Jan. 6, 2017, which designates the U.S., published in English, and claims the benefit of U.S. Provisional Application No. 62/276,422, filed on Jan. 8, 2016. The entire teachings of the above applications are incorporated herein by reference.

BACKGROUND OF THE INVENTION

Generally, the current clinically-accepted surgical paradigm for limb amputation servers discarded tissue with no thought of potential use in neural prosthetic control paradigms, and has not changed substantially in over a century. Further, there is currently no technology to restore proprioceptive feedback to thereby communicate joint and/or actuator state from a prosthesis to a patient.

Biological feedback of muscle or joint state (position and its derivatives) depends on a differential stretch signal from the spindle fibers in agonist and antagonist muscle groups acting simultaneously on the same degree of freedom [1]. For example, in the case of ankle plantar flexion, as the ankle joint plantar flexes, spindle fibers in the gastrocnemius and soleus sense muscle shortening, while spindle fibers in tibialis anterior sense muscle elongation. This differential length signal provides information to the central nervous system (brain and spinal cord) about joint position and velocity. Furthermore, force information from each muscle is communicated through biological force transducers known as Golgi tendon organs, located in the musculotendonous junction for each muscle.

Amputee patients often describe intense pain while attempting to bear weight on the distal end of their residual limbs. This pain is primarily the result of acute high stresses within the soft tissue at the distal end of the residuum, caused by large compression forces transmitted through small bony structures. In a trans-tibial amputee, for example, distal compression loads are borne by a mid-shank cross-section of the residual tibia, which is much smaller than the load-bearing bony structures in the foot. As the residuum is distally loaded, the soft tissue at the distal end of the residual limb is compressed against this small, rigid cross-section of the residual tibia, resulting in acute high stresses in the soft tissue.

Typically, development of implantable devices is currently limited by the ability to transmit power and information across the skin membrane. Wireless transmission of power is inherently inefficient, and communication often is hampered by bit-rate throttling. These obstacles are amplified as the wireless communication distance increases. Wired solutions are far superior in both bit rate and power transmission efficiency. However, concerns about infection have hindered development of wired solutions.

Neural interfacing has become an important component of systems for the rehabilitation of several disability conditions. Among these is the rehabilitation of spinal injury using "Functional Electrical Stimulation," or "FES." Using various styles of cuff electrodes, for example, developers have produced clinically useful systems that restore motor function from otherwise paralyzed muscles by electrically activating the interfaced nerves. Such systems can restore grasping ability to quadriplegic individuals [9], standing and walking to paraplegics [10], and correct foot-drop in individuals following stroke injury [11]. Aside from limb mobility, FES techniques have also been successfully applied to provide control over other motor functions such as bowel and bladder function [12], and diaphragm pacing for ventilation [13]. Furthermore, the ability to activate sensory nerves using an electrical neural interface can be applied to restoring vision in some blind populations [14].

Neuromuscular pathologies are often the result of damaged neural pathways between movement centers in the central nervous system and the skeletal muscles they control. Whether through dysfunctional contraction dynamics or muscular paralysis, this breakdown in communication renders muscles unable to produce natural movement, reducing quality of life for millions currently suffering from neuromuscular pathologies.

Therefore, a need exists for a method and system that overcomes or minimizes the above-referenced problems.

SUMMARY OF THE INVENTION

This invention generally is directed to treatment of limb pathology resulting from disease or traumatic injury and to human augmentation to enhance human physicality beyond normal physiological limits. The invention preserves post-amputation function in the residuum for the case of limb amputation, and restores natural muscle control function in paralyzed or weakened limbs due to age-related degeneration, spinal cord injury, and other neuromuscular pathologies.

In one embodiment, the invention includes restoring at least partial neuromechanical function in persons with limb loss. In one instance, a variety of possible surgical architectures serve as sliding surfaces that form a link between a mechanically-coupled agonist-antagonist muscle pair within the residual limb. In this embodiment the invention is a method of providing proprioceptive feedback in a residual limb of a person. The method of this embodiment includes forming a sliding surface within a residual limb of a person, and forming a linkage between a pair of agonist and antagonist muscles that traverses the sliding surface, whereby contraction of one of the muscles of the pair causes elongation of the other pair, thereby providing proprioceptive feedback to the person. The sliding surface can be formed at a distal end of a bone of the residual limb and may be transverse to a plane in which major longitudinal axes of the linked pair of agonist and antagonist muscles of the residual limb lie.

In a second embodiment, the invention is a method of forming a sliding surface in a partial limb of a person. The method includes the step of implanting at a bone of the partial limb an artificial support that defines a sliding surface across which linked muscles can slide. The sliding surface can be implanted at a distal end of the bone and may be transverse to a plane in which major longitudinal axes of a linked pair have agonist and antagonist muscles lie and are linked. One version of this embodiment extends this architecture to include a series of implantable osseointegrated devices.

A third embodiment includes a system that transmits load more evenly across load-bearing soft tissue of the residual limb, thereby reducing pain and discomfort during prosthetic socket loading. In this third embodiment, the invention is a method for providing proprioceptive feedback proximate to load-bearing surface area in a partial limb of person. The method includes implanting at a bone of a partial limb a device that defines a sliding surface and that also defines a load-bearing surface. The method further includes forming a linkage between a pair of agonist and antagonist muscles that traverses the sliding surface, whereby contraction of one of the muscles of the pair causes elongation of the other pair, thereby providing proprioceptive feedback to the person. The sliding surface can be transverse to a plane in which the major longitudinal axes of the linked pair of agonist and antagonist muscles lie. The load-bearing surface can be distal to the sliding surface and can have a surface area that is transverse to a major longitudinal axis of the partial limb, and that is greater than the surface of the bone at the distal end.

A fourth embodiment of the invention includes a system and method for through-skin interaction (both stimulation and recordation) with muscular architecture. In this embodiment, the invention is a system for transdermal electrical communication in a person. The system includes a percutaneous access device at a dermal surface of the person, a sensory device at at least one of a muscle and an associated nerve of the person that communicates signals between at least one of the muscle and the associated nerve, and the percutaneous access device. A stimulation device in communication with the percutaneous access device executes commands generated by the percutaneous access device.

A fifth embodiment includes an implanted system and method of closed-loop functional stimulation of muscle tissue with high fidelity feedback signals including, but not limited to, muscle position, speed and force. In this embodiment, the invention is a closed loop functional stimulation system for restoring lost functionality to a person that suffers from impairment of a neurological control system or at least partial loss of a limb. The closed loop functional stimulation system of this fifth embodiment includes a sensing system that measures at least one member of the group consisting of a length and a velocity, to generate a measured state signal of a biological structure of the person. The closed loop functional stimulation system also includes a processor that processes the measured state signal to form a controlling signal, and stimulation unit that converts the controlling signal into stimulation of a functionality related to that biological structure, thereby at least partially restoring the lost functionality to the person.

Embodiments of this invention have many advantages. For example, an embodiment of the invention provides treatment of limb pathology resulting from disease or traumatic injury by human augmentation to enhance human physicality potentially beyond normal physiological limits. In the realm of permanent assistance devices, an embodiment of the invention preserves post-amputation function in the residuum for the case of limb amputation, and restores natural muscle control function in paralyzed or weakened limbs due to age-related degeneration, spinal cord injury, or other neuromuscular pathologies.

More specifically, coupling of agonist-antagonist muscle pairs according to embodiments of the invention will enable the simultaneous control of prosthetic joint position and impedance. Further, the user will experience proprioceptive feedback of muscle fascicle strain, speed, and force. One key advantage of embodiments of the invention is bi-directional efferent-afferent neural control using biological mechanoreceptors. Further, in one embodiment, closed-loop functional simulation of the invention enables natural muscle stimulation with a gradient response using optogenetic stimulations. In addition, the framework offers closed-loop feedback of muscle fascicle length, speed and force.

The closed-loop functional stimulation system of embodiments of the invention provides repeatable control of each muscle in the agonist/antagonist pair, increasing fidelity of the perceived joint position. Muscle stimulators are inherently imprecise, and it is often difficult to model physiological response to artificial stimulation, which also often makes an open-loop stimulation paradigm difficult to manage. The closed-loop functional stimulation system of embodiments of the invention overcomes these issues, closing the loop on both force and position, to ensure that accurate position information is communicated to the prosthesis user.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4 is a schematic representation of the result of a second embodiment of a method of the invention, wherein a synthetic wrap is at a distal end of a tibia a subject to reduce sliding friction.

FIG. 5 is a schematic representation of another example of the method of the second embodiment of the invention, that includes a second muscle pair across a sliding surface of a fibula that, like the tibia, includes a synthetic wrap.

FIG. 19A is a depiction of a percutaneous access device in a dermal surface of a person, according to a system of the invention for transdermal electrical communication in a person that is a fourth embodiment of the invention.

FIG. 19B is a detail view of the percutaneous access device of FIG. 19.

FIGS. 19C-F show various examples of percutaneous access devices.

FIGS. 20A-C are different perspective views of an optical nerve cuff of the embodiment of the invention that can be employed to control a peripheral nerve.

FIGS. 20D-F are details of the perspective views of FIGS. 20A-C.

DETAILED DESCRIPTION OF THE INVENTION

Figure 2:
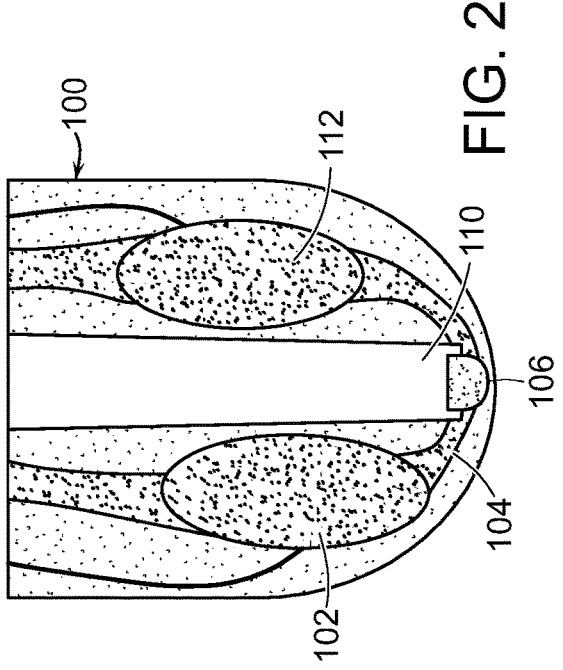
FIG. 2 is a schematic representation of the system represented in FIG. 1, formed by a method of a first embodiment of the invention wherein a linkage of agonist and antagonist muscles is formed and placed across a sliding surface of a tibia of a subject.

A description of example embodiments of the invention follows.

A first embodiment of the invention is a method of providing proprioceptive feedback of a residual limb of a subject, such as a person, that includes the steps of forming a sliding surface at a residual limb of the person and forming a linkage between a pair of agonist and antagonist muscles that traverses the sliding surface, whereby contraction of one of the muscles of the pair causes elongation of the other of the pair, thereby providing proprioceptive feedback to the person. In one embodiment, the sliding surface is formed at a distal end of the bone of the residual limb. In another embodiment the sliding surface is transverse to a plane in which major longitudinal axes of the pair of agonist and antagonist muscles of the residual limb lie. In yet another embodiment, the sliding surface is a synovial sleeve attached to a bone of the residual limb, with the agonist and antagonist muscles attached at either end of a tendon traversing the synovial sleeve, or with the agonist and antagonist muscles directly coapated to each other (e.g., fastened together) after one or both muscles are passed through the sleeve. In one embodiment, the synovial sleeve is at a side portion of the bone. In yet another embodiment, the synovial sleeve is at a distal end of the bone. In one embodiment of this method, a plurality of sliding surfaces are formed, and a plurality of pairs of agonist and antagonist muscles are linked, whereby each sliding surface supports at least one pair of muscles. In another embodiment, the sliding surface is a groove at the distal end of the bone of the residual limb. The bone can be at least a portion of at least one member of the group consisting of a tibia, a fibula, a femur, a humerus, a radius, and an ulna. The method can further include the step of forming an artificial retinaculum at the sliding surface that stabilizes the linkage of the pair of muscles at the groove. In a specific embodiment the artificial retinaculum is formed of a synthetic material. Alternatively, the artificial retinaculum is formed of at least one tissue selected from the group consisting of tendon and ligament. In still another version of this embodiment, the method further includes the step of wrapping the distal end of the bone with the material to secure the linkage of the muscle pair at the distal end of the bone, while allowing sliding of the linkage across the sliding surface. In one version of this embodiment, the method further includes at least one step selected from the group consisting of forming a groove at the distal end of the bone to thereby form the sliding surface, and forming one or more artificial retinacula at the sliding surface that stabilize(s) the pair of muscles of the groove. Retinacula material can be formed, for example, of a suitable synthetic material, as is known in the art, such as at least one member of the group consisting of titanium, silicone, plastic, a chromium cobalt alloy, and a ceramic. In still another embodiment, the bone is at least a portion of a tibia and a fibula, and the sliding surface is formed by constructing the tibia-fibula bridge between distal ends of the tibia and fibula, whereby the tibia and fibula bridge defines the sliding surface. In one such embodiment, the bride is an osseous bridge, or, alternatively, the bridge can be a tendonous bridge. The sliding surface, in one embodiment, can support a plurality of linkages, between agonist and antagonist muscles. In another embodiment, the sliding surface is defined by a tendonous ring fixed to the distal end of the residual limb, such as the distal end of a bone. In another embodiment, the agonist and antagonist muscles are linked by at least one member of the group consisting of a muscle tissue, a tendon, and a synthetic material.

In a second embodiment of the invention, a method of forming a sliding surface in a partial limb of a subject includes the step of implanting at the bone of the partial limb an artificial support that defines sliding surface across which the linked muscles slide. In one such embodiment, the artificial support is a ring, such as a ring that is osseointegrated into the bone. In another alternative, the artificial support includes at least one member selected the group consisting of a groove, a notch, and a channel, any of which can be osseointegrated into the bone. Alternatively, the artificial support includes a fixture implanted into the bone, a pylon extending distally from the fixture, and at least one member of the group consisting of a ring, a groove, a notch and a channel at the artificial support. In this embodiment, the fixture can, for example, be osseointegrated into the bone, and the pylon can be percutaneous. In one version of this embodiment, the agonist and antagonist muscles are linked by at least one member of the group consisting of muscle tissue, tendon, and synthetic material.

In a third embodiment of the invention, a method for providing proprioceptive feedback proximate to a load-bearing surface area in a partial limb of a subject includes the steps of: implanting at a bone of a partial limb a device that defines a sliding surface and that defines a load-bearing surface (e.g. a load-bearing surface distal to the sliding surface), and forming a linkage between a pair of agonist and antagonist muscles that traverses the sliding surface, whereby contraction of one of the muscles of the pair causes elongation of the other of the pair, thereby providing proprioceptive feedback to the subject. The load-bearing surface can have a surface area that is transverse to a major longitudinal axis of the partial limb and that is greater than the surface area of the bone at the distal end. In one version of this embodiment, the sliding surface is defined by a fixture at a distal end of the bone, such as a fixture that is osseointegrated into the bone. In one version of this embodiment, the load-bearing surface is defined by a distal load-bearing attachment at the fixture, such as a load-bearing attachment that includes a proximal and a distal end, wherein the distal end has a lower mechanical impedance than the proximal end. In this embodiment, the distal load-bearing attachment can include a first component that includes a proximal end and a second component that includes the distal end. The first and second components can be at least a portion of a laminate. In another embodiment, the fixture includes a ring that defines the sliding surface, such as a fixture that is osseointegrated into the bone. In one specific embodiment, the bone is at least a portion of a tibia.

In a fourth embodiment of the invention, a system for transdermal electrical communication in a subject includes: a percutaneous access device at a dermal surface of the subject; a sensory device at at least one of a muscle and associated nerve of the subject that communicates signals between at least one of the muscle and the associated nerve, and the percutaneous access device; and a stimulation device in communication with the percutaneous access device that executes commands generated by a percutaneous access device. In a specific version of this embodiment, communication between the percutaneous access device and the sensory device is bidirectional. The sensory device can include at least one member of the group consisting of a receiver, a transmitter and a transceiver. The sensory device can include at least one member of the group consisting of an electrode, a sonomicrometry crystal, a nerve cuff, and a nerve array, such as a nerve array that includes at least one member of the group consisting of a microchannel nerve array, a powered nerve array, a silicon-based microelectrode array such as a Utah slanted electrode array, and an array of fine wires. In another version of the fourth embodiment of the invention, the percutaneous access device includes a memory and circuitry that stores signals from the sensory device in the memory. The percutaneous access device can include circuitry that processes signals received from the sensory device. In one embodiment, the processing circuit includes at least one member of the group consisting of filtering, band limiting, modeling, functional electrical stimulation control, and functional optical stimulation control. In one specific version, the percutaneous access device includes circuitry that transmits signals wirelessly. A version of this embodiment of the invention can, optionally, include a plurality of percutaneous access devices, such as wherein at least a portion of the percutaneous access devices are networked with each other. In another version of this embodiment of the invention, the actuation device is at least one member selected from the group consisting of a motorized prosthesis, a motorized orthosis, a motorized exoskeleton, and a module that functionally stimulates muscle tissue. For example, the actuation device can be a module that functionally stimulates muscle tissue. In one specific embodiment, the actuation device includes at least one member of the group consisting of an optogenetic stimulator, and a functional electrical stimulator. In one version of this embodiment of the invention, the percutaneous access device is a portal for wires extending through a body surface.

In another embodiment of the invention, a closed loop functional stimulation system for restoring lost functionality to a subject that suffers from impairment of a neurological control system with at least partial loss of a limb includes: a sensing system that measures at least one member of the group consisting of a length and a velocity, to generate a measured state signal of a biological structure of the subject; a processor that processes the measured state signal to form a controlling signal; and a stimulation unit that converts the controlling signal into stimulation of a functionality related to the biological structure, thereby at least partially restoring the lost functionality to the subject. In one version of this embodiment, the biological structure is a muscle and the sensing system includes a fascicle state sensor that measures length and the velocity of the muscle, and may also include a force sensor that measures force of the muscle, whereby the processor converts the controlling signal into at least one of stimulation of the muscle that at least partially restores the lost functionality to the subject. In a specific version of this embodiment, the system further includes a percutaneous access device that provides afferent feedback to the processor to form the controlling signal. In another version, the sensing system is employed to provide control over at least one of a motorized prosthesis, a motorized orthosis, a motorized exoskeleton, and a module that functionally stimulates muscle tissue. The system can further include at least one sensor on at least one of the motorized prosthesis, motorized orthosis, and motorized exoskeleton, the sensor configured to send information to the processor to modify the controlling signal. In an embodiment, the system further includes an external sensing system that measures at least one of a contact force (e.g., ground reaction force), a skin strain, a pressure and a shear force; and a sensory conversion processor that converts the measurement of the external sensing system to a stimulation signal to selectively stimulate one or more afferent nerves of the subject. In another version, the system further includes a neurally modulated reflex gaining unit that carries an efferent signal from the central nervous system of the subject to the processor, whereby the controlling signal is modulated. In still another version, the neurally-modulated reflex gain unit modulates joint torque and position of the neuromuscular model of the processor forming the controlling signal. In one such specific version, the neurally-modulated reflex gain unit includes: an activation dynamics unit that employs an efferent signal from the subject to generate an activation dynamics signal; a muscle attachment geometry model that processes a joint state of an external prosthesis linked to the biological structure to thereby generate a muscle attachment geometry signal; and a muscle-tendon complex model that converts the activation dynamics signal and the muscle attachment geometry signal to thereby generate a command signal that is communicated to the external prosthesis. In an alternative version of this embodiment, the biological structure is a muscle and the processor includes: an activation model module that processes an electromyographic signal from the muscle and thereby generates an activation signal; a neuromuscular model module that processes a measured state signal of the muscle and the activation signature to thereby estimate the force and state of the muscle; and a reflex model module that processes the estimated force and the state of the muscle to thereby generate the controlling signal. In a specific version, the stimulation unit is at least one member of the group consisting of an optogenetic stimulator, and an electrical stimulator. In one embodiment, the biological structure includes a pair of agonist and antagonist muscles that are linked across a sliding surface at a residual limb of the subject, whereby contraction of one of the muscles of the pair causes elongation of the other of the pair, thereby providing proprioceptive feedback to the subject.

It should be noted that different embodiments and components of the invention can be combined. Examples given herein refer to single amputation levels in the lower limbs, but application can also be made to other limbs and amputation levels.

Embodiment 1: Mechanical Coupling of Agonist-Antagonist Residual Muscle Pairs Across Surgically Constructed Sliding Surfaces A first embodiment of this invention is a method that constructs an architecture in the residual musculature that can be used to provide proprioceptive feedback from an external limb prosthesis.

In this embodiment, the invention includes a method for reconstructing the biological proprioceptive feedback paradigm in a subject, such as a person, with limb amputation. The method includes mechanically linking the distal ends of residual musculature across a sliding surface, so that contraction of the agonist muscle causes stretching of the antagonist and vice versa. By allowing such an agonist-antagonist interaction, the antagonist muscle that is stretched provides length, speed and force proprioceptive feedback to the amputee user, via each muscle nerve supply, to communicate muscle action and joint movement. Alternatively, when the antagonist muscle contracts, the agonist muscle is elongated, providing proprioceptive feedback communicating the opposite movement direction. This approach takes advantage of existing neural pathways to communicate joint position information with the prosthesis user, namely a person or other subject, enabling amputees to better interact with their prostheses.

The method of this embodiment of the invention can employ at least one of several methodologies through which coupling can be achieved surgically, including, for example, at least one member of the group consisting of: direct end-to-end suturing; forming a tendon bridge in which the distal end of each muscle is sutured to either side of a tendon segment; and forming a synthetic bridge, to which the distal end of each muscle is attached.

Figure 3:
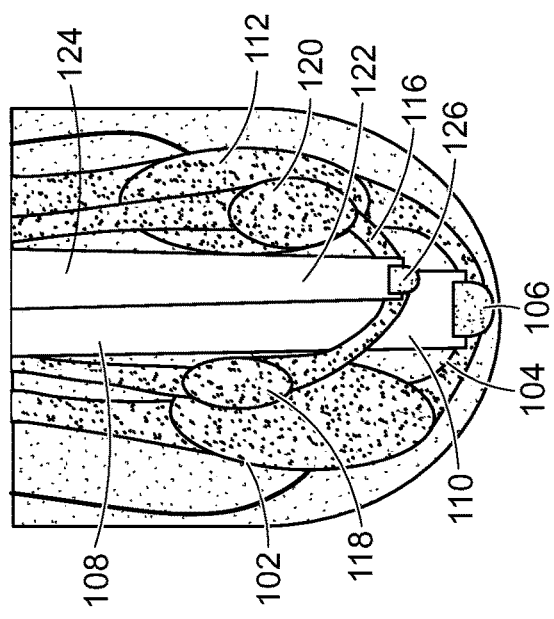
FIG. 3 is a schematic representation of the results of a first embodiment of the method of the invention that further includes an additional step of forming a linkage of agonist and antagonist muscles across an end portion of a fibula of a subject.
Figure 1:
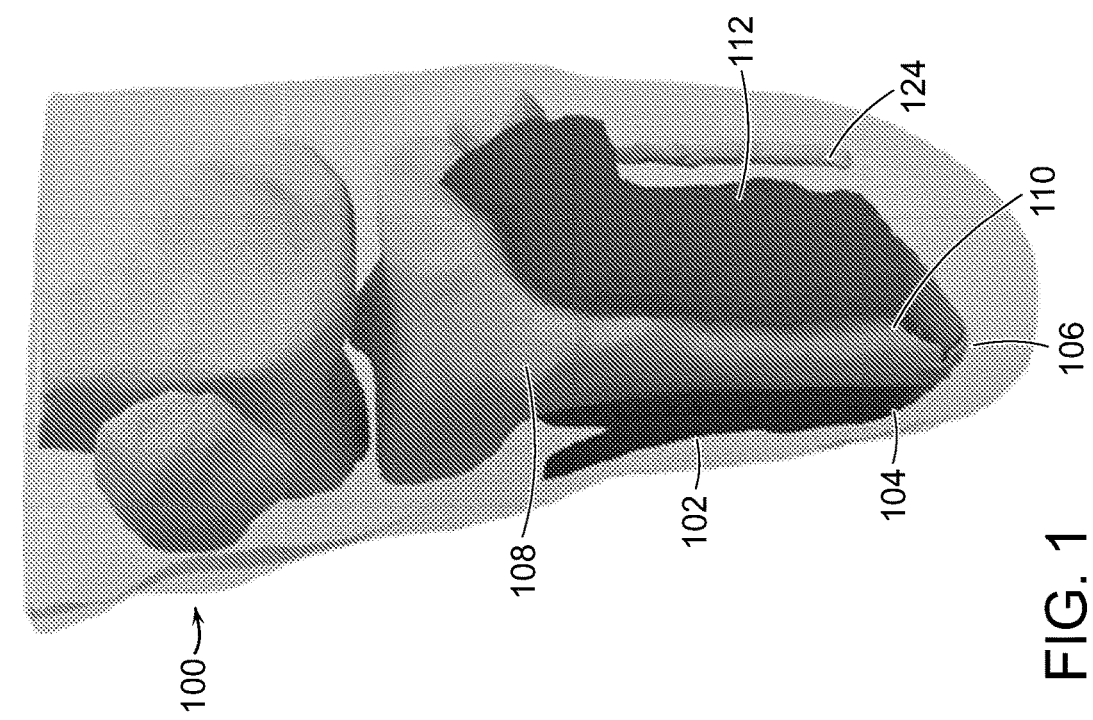
FIG. 1 is a three-dimensional representation of a system formed by a method of a first embodiment of the invention for providing proprioceptive feedback in a residual limb of a subject.

One version of the method of this embodiment of the invention includes a surgically-constructed sliding surface for a coupled agonist/antagonist muscle pairing. Examples of surgically-constructing a sliding surfaces according to a method of the invention include the following five procedures:

1. Carving grooves into a distal end of native skeletal architecture of a subject. In transtibial amputation, for example, grooves are carved in a distal end of the tibia and fibula that serve as sliding surfaces for any number of coupled muscle pairings. In one example, artificial retinacula are constructed either from tissues harvested during the amputation or from synthetic materials, and placed across the grooves to secure soft tissue. Optionally, the bone tissue at the distal end is wrapped in a synthetic material to promote frictionless sliding of the linked muscle pair across the grove. As shown in FIG. 1, for example, a system in subject 100 formed by the method of the invention includes the following elements: agonist muscle 102, linkage 104 made of muscle, tendon, or synthetic material; tendonous or synthetic retinaculum 106, severed tibia 108 with grooved distal end 110, and antagonist muscle 112. By allowing sliding across grooved distal end 108, when agonist muscle 102 contracts, antagonist muscle 112 thereby stretches providing length, speed and force proprioceptive feedback to amputee subject 100 by way of the nerve supply of each muscle, to communicate muscle action and joint movement. Conversely, when antagonist muscle 112 contracts, agonist muscle 102 is elongated, thereby providing proprioceptive feedback communicating the opposite movement direction to subject 100. FIG. 2 is a schematic representation of the results of the embodiment represented in FIG. 1. FIG. 3 is a schematic representation of the results of another version of this embodiment of the method of the invention that further includes an additional step of forming a linkage 116 of agonist 118 and antagonist 120 muscles across an end portion 122 of fibula 124 of the subject 100. Retinaculum 126 is placed across linkage 116.

Examples of pairs of muscles that may be linked in the transtibial amputation case include: 1) tibialis anterior and gastrocnemius, 2) peroneus longus and tibialis posterior, and 3) extensor digitorum longus and flexor digitorum longus. It will be understood that other pairs of muscles of may be linked.

FIG. 4 is a schematic representation of the result of another version of the first embodiment of the invention, wherein synthetic wrap 128 is at distal end of tibia 108 to reduce sliding friction. Synthetic wrap 128 can be constructed from any suitable biocompatible material known to those skilled in the art. For example, titanium can be employed. Other examples include a chromium cobalt alloy and ceramic. FIG. 5 is a schematic representation of another example, where the method of the invention may be expanded to include multiple muscle pairings, including a second agonist/antagonist muscle pair 116, 118 connected by linkage 116 across a sliding surface of fibula 124 that, like tibia 108, includes a synthetic wrap, such as synthetic wrap 130, as shown.

Figure 6:
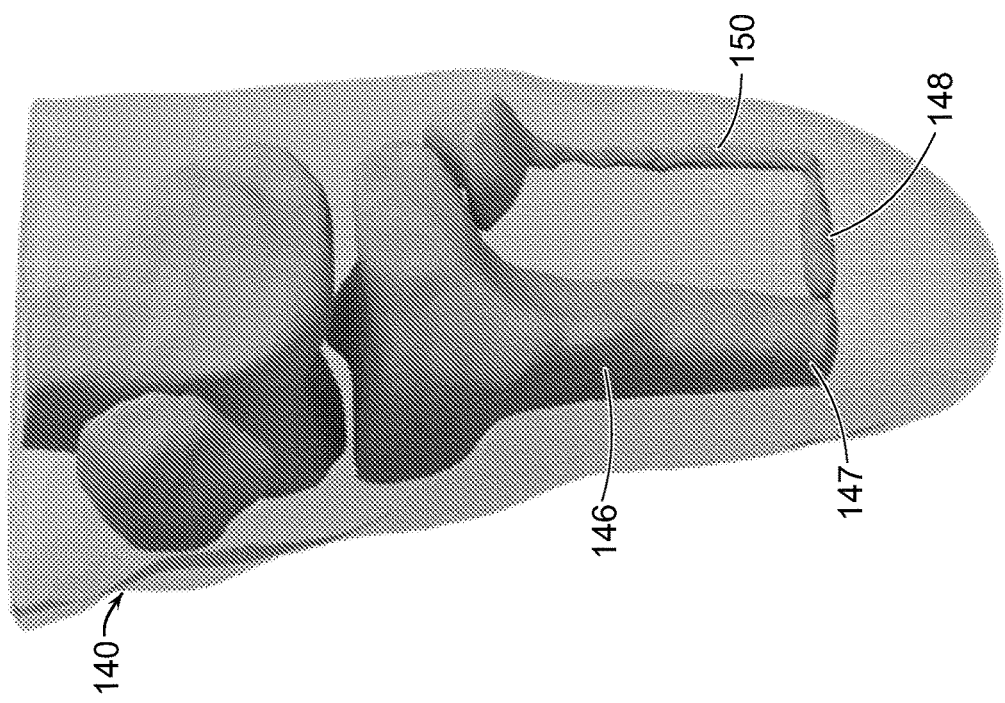
FIG. 6 is a three-dimensional representation of the result of an embodiment of the method of the first embodiment of the invention, wherein an osseous or tendonous bridge is formed that serves as a sliding surface for at least one coupled agonist/antagonist muscle pair.
Figure 7:
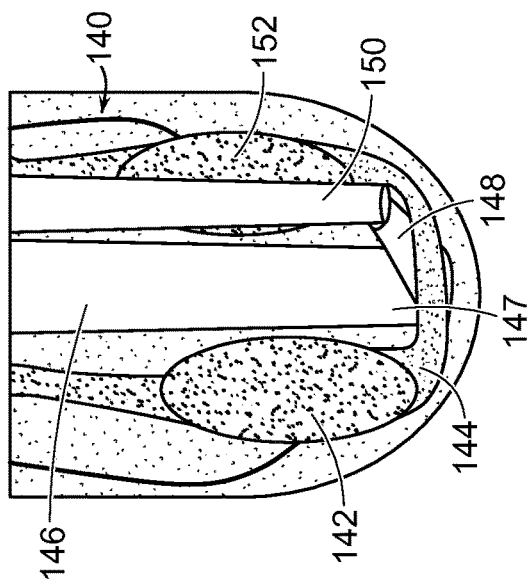
FIG. 7 is a schematic representation of the embodiment shown in FIG. 6, wherein a single muscle pairing traverses the osseous or tendonous bridge.
Figure 8:
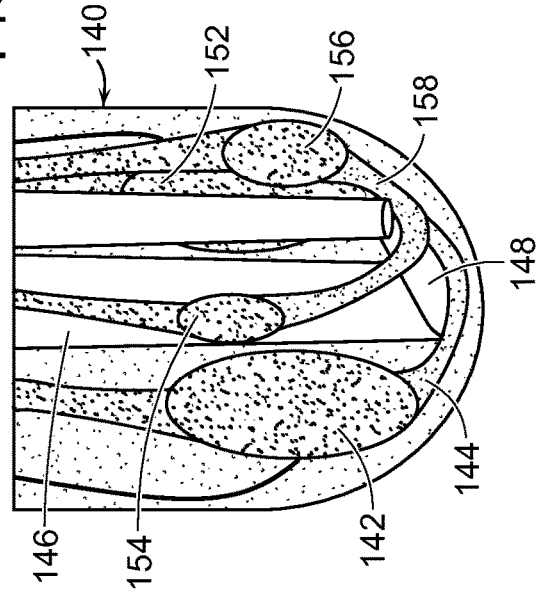
FIG. 8 is a schematic representation of the embodiment shown in FIG. 6, wherein a plurality of agonist/antagonist muscle pairs traverses an osseous or tendonous bridge surface.

2. Forming an osseous tibia-fibular bridge. In this embodiment, at least one osseous tibia-fibular bridge is formed to provide a sliding surface for one-or-multiple linked agonist/antagonist muscle pairs. Optionally, grooves and retinacula, as described above can be added to the at least one osseous bridge. In one embodiment, a synthetic wrap is formed at the osseous bridge tissue to promote sliding. Although shown with reference to a trans-tibial amputee, the method of the invention can be applied to a trans-radial amputee. FIG. 6 is a representation of an osseous tibia-fibular bridge formed in one embodiment of the method of this invention. FIG. 7 is a schematic representation of one embodiment of a single muscle pairing in the transtibial amputee mode. FIG. 8 is a schematic representation of how this embodiment of the method of the invention can include multiple muscle pairings. The system formed in subject 140 by this embodiment of the method of the invention includes: agonist muscle 142, linkage 144 made of muscle, tendon, or synthetic material; tibia 146; osseous tibia-fibula bridge 148; fibula 150; and antagonist muscle 152. In the example shown, the osseous tibia-fibula bridge is formed at a distal end 147 of tibia 146. As shown in FIG. 8, a second pair of agonist 154 and antagonist 156 muscles connected by tendonous linkage 158 can span osseous tibio-fibular bridge 148.

3. Forming a tendonous tibio-fibular bridge. In this embodiment of the method of the invention, at least one tendonous, rather than an osseous tibio-fibular bridge is formed and employed as a sliding surface for one or multiple linked agonist-antagonist muscle pairs. Another example of the embodiment of the method of the invention is application to a trans-radial amputee.

4. Forming tendonous rings sutured to periosteum. Another embodiment of the invention includes forming at least one tendonous ring or loop that is sutured to bone or other rigid biological tissue to form a sliding surface for at least linked one pair of agonist-antagonist muscles.

5. Securing a synovial sleeve to bone or other rigid biological material. Another embodiment of the invention includes surgical attachment of a synovial tunnel (e.g., synovial sleeve or synovial sheath) sutured to bone or other rigid biological tissue to form a sliding surface for at least one pair of linked agonist-antagonist muscles. The agonist and antagonist muscles can be attached at either end of a ligament or tendon traversing the synovial sleeve, or can be directly coapted to each other (e.g., fastened together) after one or both muscles are passed through the sleeve.

Figure 36:
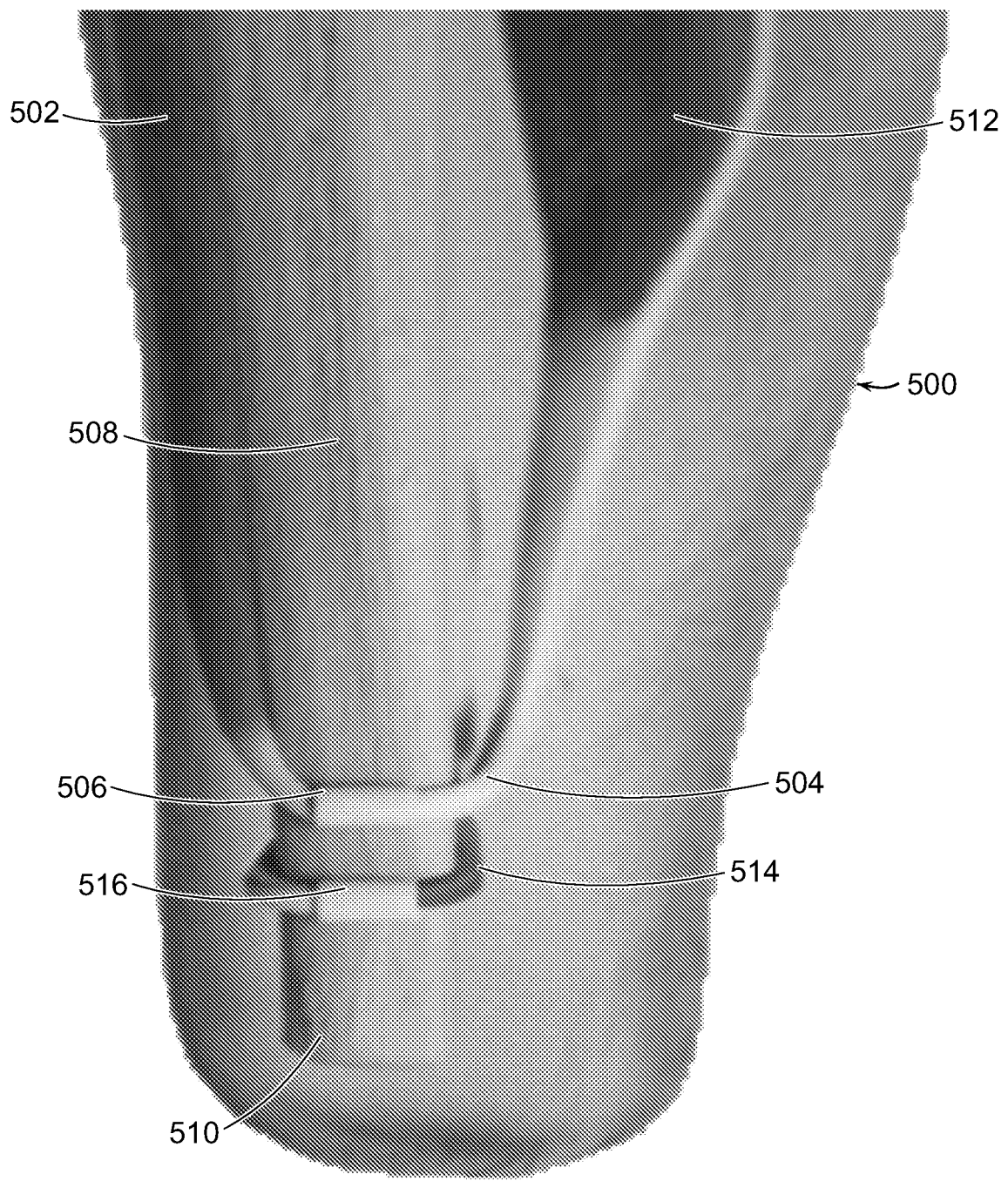
FIG. 36 is a three-dimensional representation of the result of an embodiment of the method of the first embodiment of the invention, wherein two synovial sleeves are formed that serve as sliding surfaces for coupled agonist/antagonist muscle pairs.

FIG. 36 is a three-dimensional representation of the result of an embodiment of the method of the first embodiment of the invention, wherein one or more synovial sleeves are formed that serve as sliding surfaces for coupled agonist/antagonist muscle pairs. The system formed in subject 500 by this embodiment of the method of the invention includes: agonist muscle 502, linkage 504 traversing synovial sleeve 506 at bone 508, and antagonist muscle 512. Optionally, the embodiment includes a second synovial sleeve 516 carrying a second linkage 514 of a second pair of muscles (not shown). In the example shown, the synovial sleeves 506 and 516 are positioned at a side of bone 508. Although the sleeves are shown as being positioned on the same side of bone 508, they need not be. Further, the sleeves may be positioned at distal end 510 of bone 508.

The synovial sheath can be harvested from amputated joints. For example, in a below-knee amputation, synovial sheaths could be taken from the ankle joint, and would include (for instance) the tarsal tunnels. These sheaths exist at every joint in the body, and provide protected routing of tendons as they cross joints. Several examples of coaptation methodologies exist. In one embodiment, the native tendon is left in the canal formed by the sheath, and muscles are sutured to either end of the native tendon. It is also be possible to remove the native tendon from the canal, thread either the agonist or the antagonist muscle through the canal by passing one end of the muscle from one side of the canal through the canal to another side of the canal, and coapting the muscles near the other side of the canal. It is also possible to use a biological or synthetic tendon-like material to traverse the canal, in place of the native tendon. A synthetic canal replacement could be made of silicone and used in place of the canal.

Figure 10:
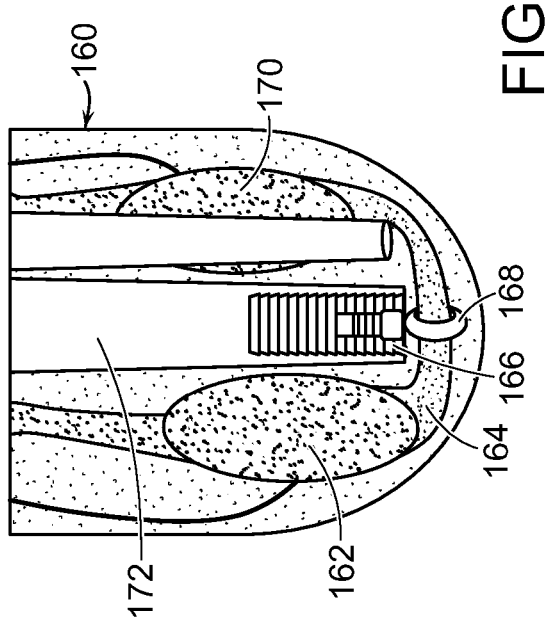
FIG. 10 is a schematic representation of the product of the method of the second embodiment, represented in FIG. 9.
Figure 11:
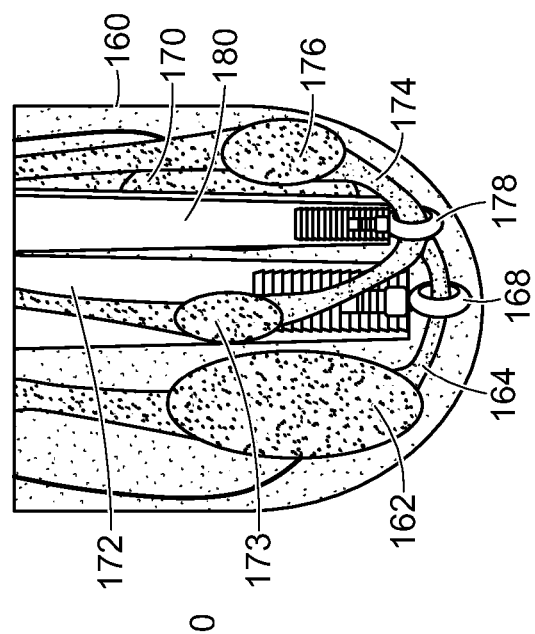
FIG. 11 is a schematic presentation of two pairs of agonist/antagonist muscles coupled through rings osseointegrated into the distal end of each of a tibia and a fibula of a subject.
Figure 9:
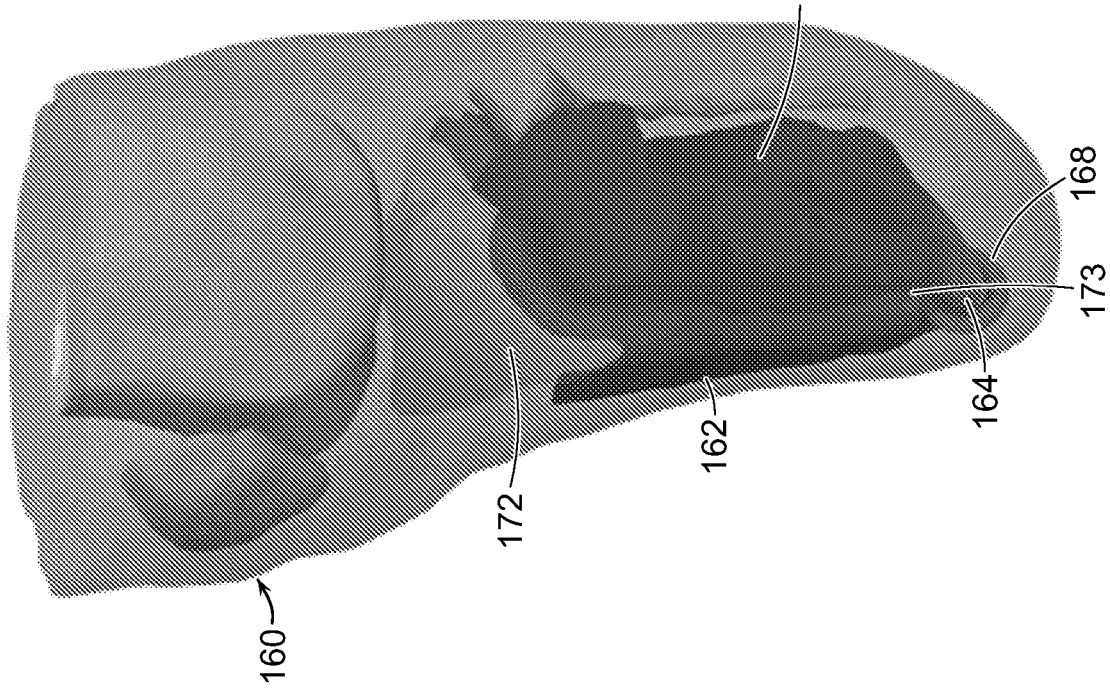
FIG. 9 is a three-dimensional representation of the product of a method that is a second embodiment of the invention, wherein an agonist/antagonist muscle pair is coupled through a single ring that is osseointegrated into a distal end of a tibia of a subject.

Embodiment 2: Forming an Osseointegrated Sliding Surface for Mechanically-Coupled Agonist-Antagonist Muscle Pairs Osseointegration is a proven methodology that has existed for years in the fields of medical dentistry, orthopedic surgery, and prosthetic technology. The core principle involves insertion of a biologically inert synthetic material into porous bone tissue. The body's natural reaction to the foreign material causes integration of the living tissue and the synthetic insert, forming a robust mechanical bond. In this embodiment of the invention, sliding surfaces for mechanically-coupled agonist-antagonist muscle pairs are secured to the distal end of a bone, such as a tibia or a fibula, by osseointegration. Exemplary versions of this embodiment of the invention include:

1. Forming rings. Muscle couplings, whether made of muscle, tendon, or a synthetic material, slide through rings formed by osseointegration into the distal end of the bone, which thereby inherently prevent dislodgement of the coupling from the sliding surface, and protect the coupling from compression that may prevent sliding or damage of the tissue. FIGS. 9 and 10 show embodiments of systems formed by employing a single ring and a muscle pairing in the trans-tibial amputee model, one example of how the system can be expanded to include multiple rings and muscle pairings. One system formed in subject 160 by this embodiment of the method of the invention includes the following elements: agonist muscle 162, linkage 164 made of muscle, tendons, or synthetic material; osseointegrated titanium fixture 166; synthetic ring 168, and antagonist muscle 170 at tibia 172. In the example shown, ring 168 is at distal end 173 of tibia 172. In one specific version of this embodiment, shown in FIG. 11, second agonist muscle 173 is connected by linkage 174 to antagonist muscle 176 through ring 178 that is osseointegrated into fibula 180.

Figures 12, 12A:
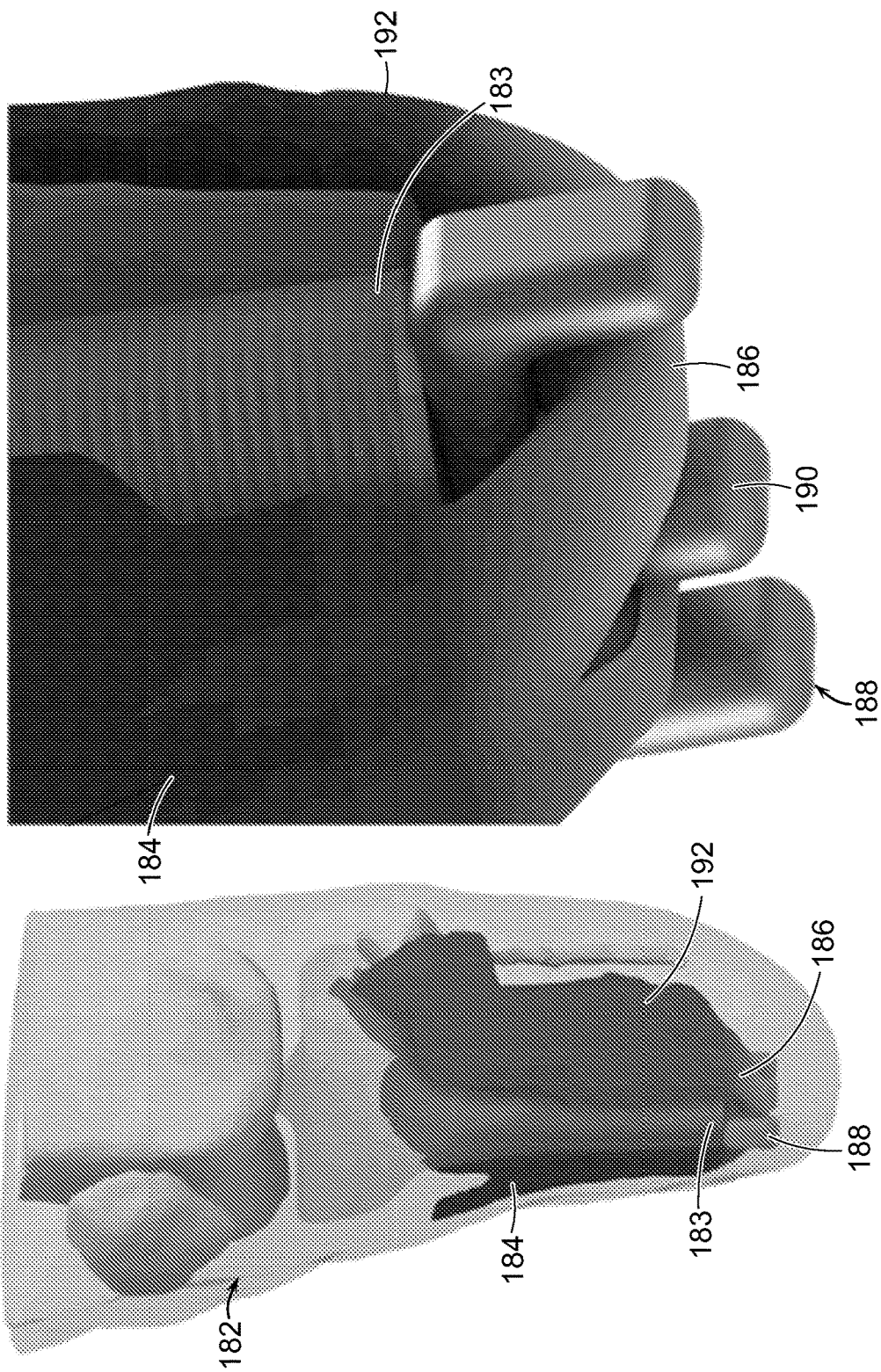
FIG. 12 is a three-dimensional representation of the product of the method of the second embodiment of the invention, wherein agonist/antagonist muscles are coupled and traverse a smooth surface of osseointegrated grooves or notches.
FIG. 12A is a detail of the representation shown in FIG. 12.

2. Forming grooves, notches, or channels. As a result of another version of this embodiment of the method of the invention, muscle couplings slide through at least one osseointegrated structure with grooves, notches, or channels. As shown in FIGS. 12 and 12A, the system in subject 182 formed by this version of this embodiment of the method of the invention includes: agonist muscle 184, linkage 186 made of muscle, tendon, or synthetic material; osseointegrated titanium fixture 188 secured in bone 183, synthetic grooves or notches 190, and antagonist muscle 192.

Figure 13A:
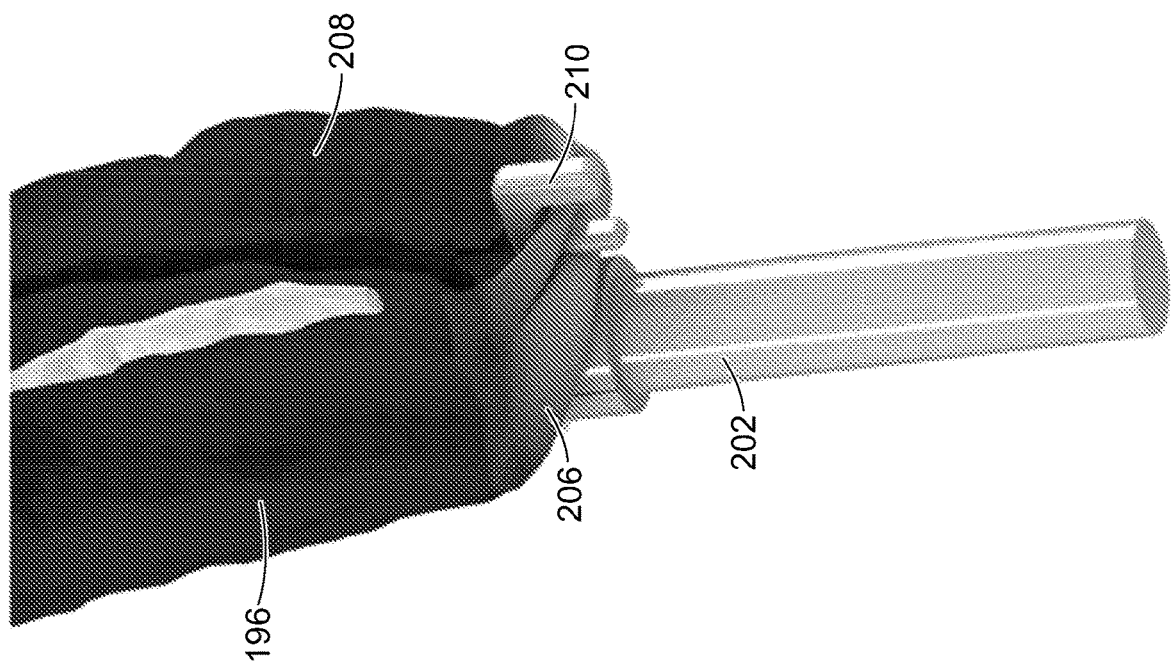
FIG. 13A a posterior view of a detail of the three-dimensional representation shown in FIG. 13.
Figure 13:
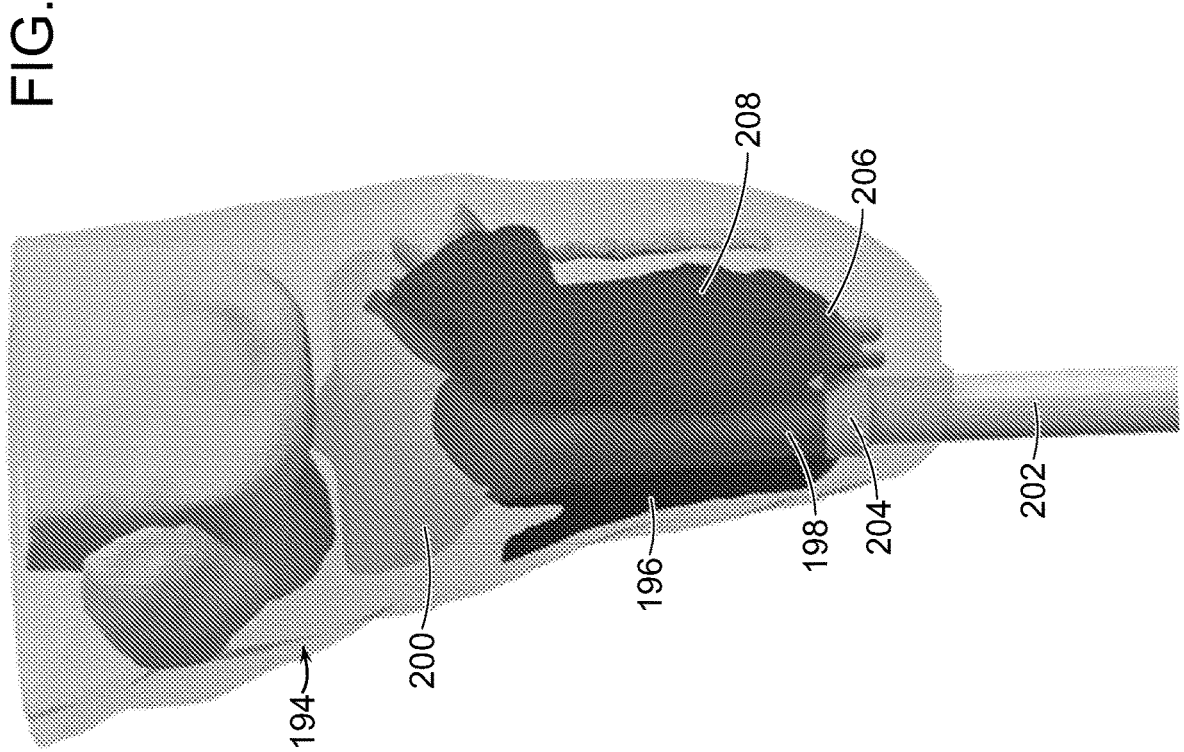
FIG. 13 is a three-dimensional representation of the product of a second embodiment of the method of the invention, wherein a collar is affixed to a percutaneous osseointegrated pylon that provides one or multiple sliding services for one or more coupled agonist/antagonist muscle pairs.

3. Forming a collar for a percutaneous osseointegrated pylon. In patient cases where an osseointegrated pylon for direct skeletal attachment of prostheses is in place or will be implanted, the method of the invention can include adding one or multiple collars with rings, grooves, notches, or channels to the extra-osseous segment of the pylon. The rings, grooves, notches, or channels in the collar(s) serve as sliding surfaces for one or multiple linked muscle pairings. As shown in FIGS. 13 and 13A, the system formed in subject 194 by this version of the embodiment of the method of the invention includes: agonist muscle 196; osseointegrated titanium fixture 198 in tibia 200; percutaneous osseointegrated pylon 202, collar 204, linkage 206 made of muscle, tendon, or synthetic material; antagonist muscle 208; and groove or notch 210 of osseointegrated fixture 198.

Embodiment 3: Forming an Osseointegrated Distal Load-Bearing Attachment

Another embodiment of the method of the invention includes embedding an implant in the residual limb to broaden the load-bearing surface of the distal residuum and thereby spread relatively high compression forces across a larger load-bearing surface.

Figure 15:
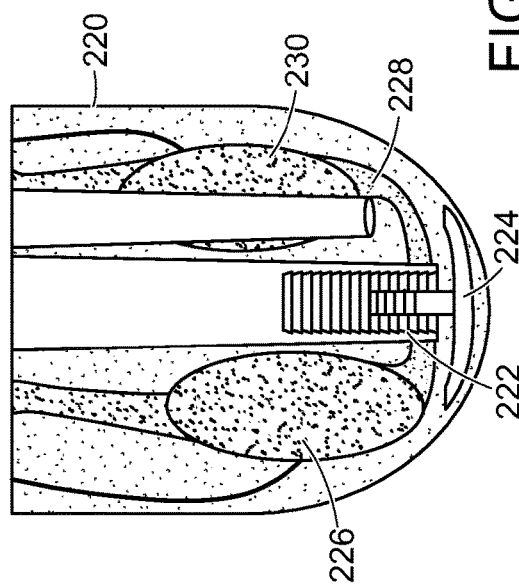
FIG. 15 is a schematic representation of the three-dimensional representation shown in FIG. 14.
Figure 16:
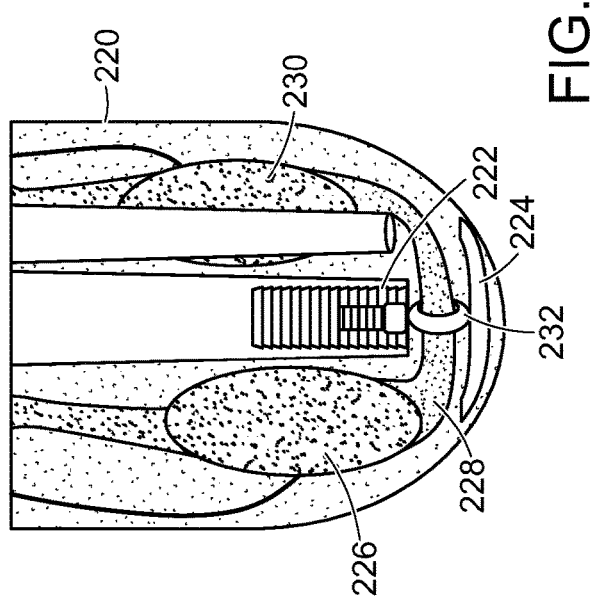
FIG. 16 is a schematic representation of the product formed by the third embodiment of the method of the invention, further including a ring, through which the agonist/antagonist muscle pair are coupled.
Figure 14:
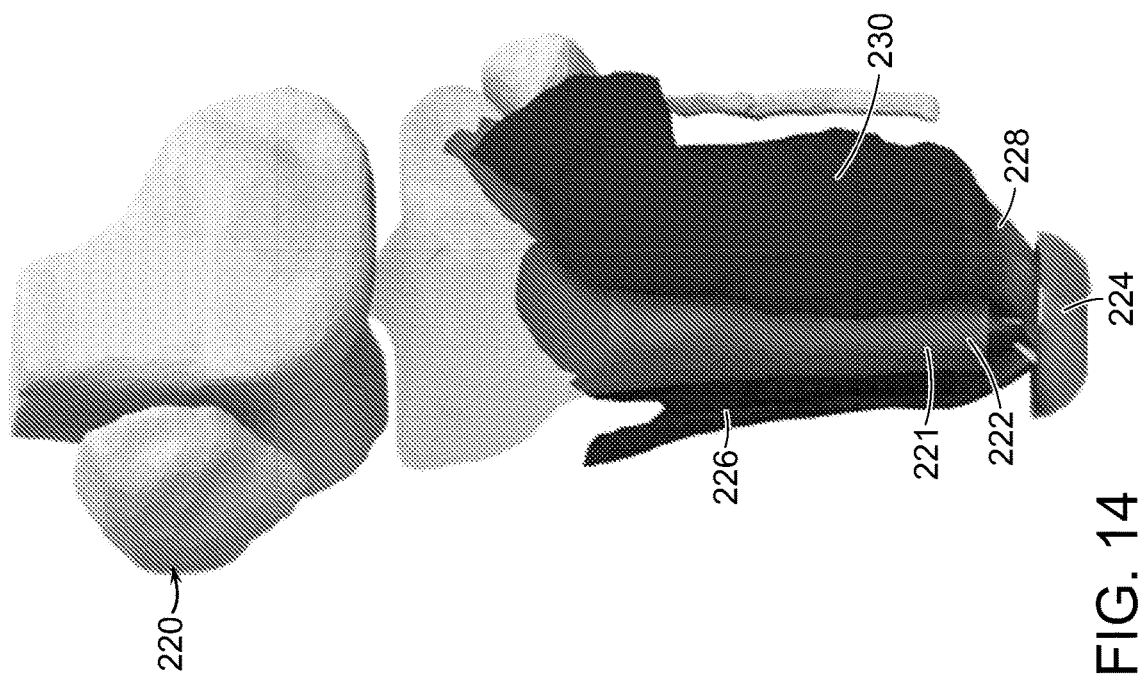
FIG. 14 is a three-dimensional representation of the product of a third embodiment of the method of the invention, wherein an osseointegrated structure is geometrically shaped to increase cutaneous load-bearing surface area.

In this embodiment of the method of the invention, an extension (either biologic or synthetic) is embedded in the skeletal system to increase comfort in compressive distal load-bearing. Two examples of this embodiment of the invention are described below:

1. Osseointegrating a structure that is shaped geometrically to increase load-bearing surface area. Concentrated areas of high pressure are eliminated by increasing the surface area through which the compressive load is transmitted. FIG. 14 shows an example of a system formed by this embodiment of the method of the invention. FIGS. 15 and 16 show examples of how the system may be combined with a synthetic sliding surface attachment. This system in subject 220 includes: osseointegrated titanium fixture 222 at tibia 221; and synthetic load-bearing attachment 224. When combined with a synthetic sliding surface attachment, other relevant components of the system formed by the method of the invention include: agonist muscle 226; linkage 228 made of muscle; tendon, or synthetic material; and antagonist muscle 230. Optionally, as shown in FIG. 16, ring 232 is between osseointegrated fixture 222 and load-bearing attachment 224 and acts as a sliding surface for linkage 228.

Figure 17:
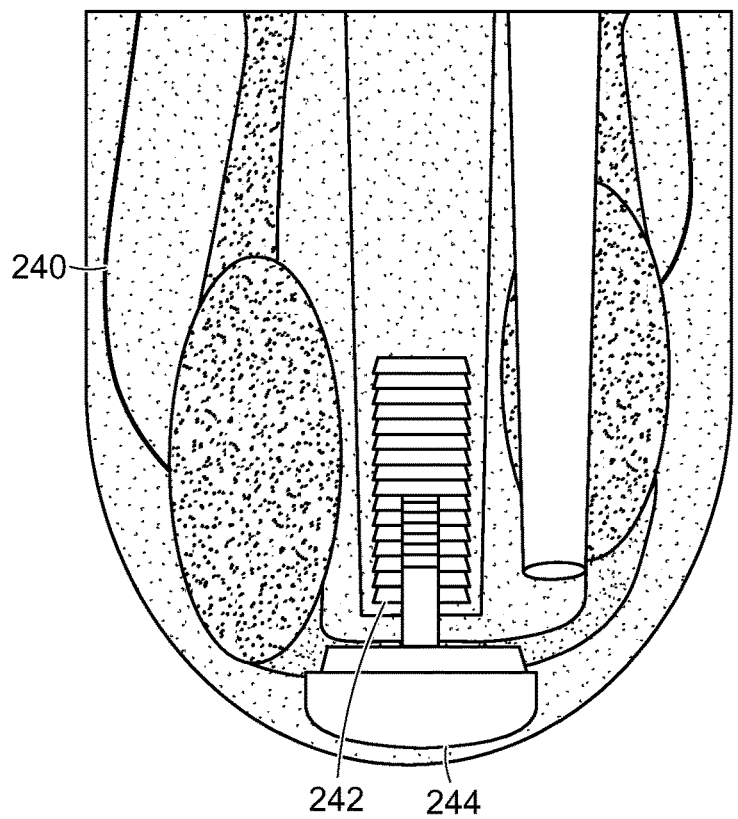
FIG. 17 is a schematic representation of the product of a method of the third embodiment of the invention, wherein an osseointegrated load-bearing surface is made of multiple materials of different mechanical impedances, to dissipate distal shock waves.
Figure 18:
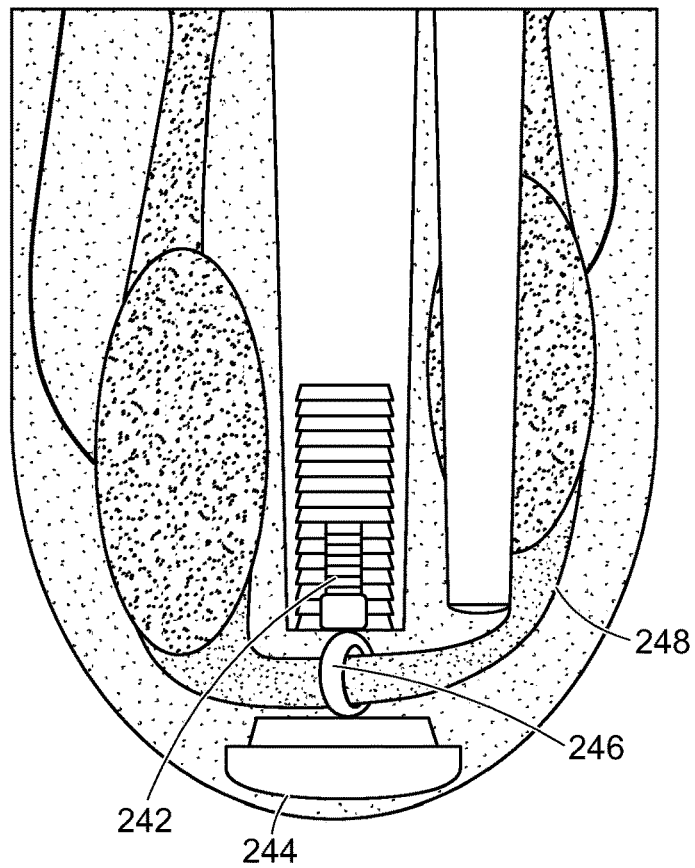
FIG. 18 is a schematic representation of a product formed by a third embodiment of the method of the invention, wherein the osseointegrated load-bearing surface is made of multiple materials of different mechanical impedances, and wherein the pair of agonist/antagonist muscles are coupled through a ring component of the osseointegrated load-bearing surface.

2. Osseointegrating a structure comprised of one or multiple materials that transition from stiff to soft in the distal direction. Another version of this embodiment of the method of the invention allows for dissipation of relatively high-compressive forces and shock loads. FIG. 17 shows one version of this embodiment of a system formed by the embodiment of the method of the invention. FIG. 18 shows one example of how the system may be combined with a synthetic sliding surface attachment. The system formed in subject 240 by the method of the embodiment of the invention includes: osseointegrated titanium fixture 242; and synthetic load-bearing attachment 244 made from one or multiple materials that transition from stiff to soft in the distal direction. Optionally, as shown in FIG. 18, ring 246 is located between osseointegrated titanium fixture 242 and synthetic load-bearing attachment 244 and acts as a sliding surface for a linkage between an agonist/antagonist muscle pair 248. Synthetic load-bearing attachment 244 includes a high-mechanical-impedance material comparable to titanium fixture on upper, proximal end, but which becomes increasingly compliant in the distal direction, assuming a relatively soft mechanical compliance comparable to human skin at the distal aspect of attachment, or the attachment-skin interface. Through this multiple-material design, distal shock loads can be effectively dissipated to further mitigate discomfort experienced by the amputee patient upon load-bearing.

Embodiment 4: A Communication Paradigm for Through-Skin Electrical Signal Transmission One embodiment of this invention provides benefits of a wired solution for implantable devices, while largely avoiding the infection problem. In one embodiment, the invention includes a system in which data is communicated bi-directionally from implanted passive devices, such as wired electrodes, sonomicrometry crystals, optical nerve cuffs, microchannel nerve arrays, and nerve arrays, to power electronics outside of the body by way of a suitable anti-infection percutaneous access device (PAD), such as the one developed by Viaderm, LLC, which was originally developed to be a component of the CardioVAD Left Ventricular Assist Device system (LVAD Technology, Inc.) [7], or as otherwise known to those skilled in the art.

In one embodiment, the invention includes, at least in part, two medical devices: a percutaneous access device, such as described above [2], and wired electrodes for limb musculature [3-6]. Wired muscle electrode technology has been approved by the FDA for the treatment of other indications and has been employed within the United States for decades. This embodiment of the invention combines these two established technologies with additional technological components, for use in long-term electrophysiological access to residual musculature in persons with limb pathology. Sonomicrometry crystals, for example, provide robust, long-term access to direct measurements of muscle fascicle length and velocity. Although not yet approved for human use, their viability in vivo has been demonstrated in longitudinal studies in several animal models [8]. Microchannel nerve arrays, as another example of additional components that can be employed by the invention, provide high-resolution electrical access to the axons that make up a nerve bundle. Optical nerve cuffs, as a third example, deliver light to nerve fascicles that are genetically modified to trigger action potentials in response to light in the visible spectrum.

In this embodiment of the invention, analog signals from the at least one of the implanted passive electronic devices, are amplified and digitized onboard an external power electronics of the PAD (herein referred to as a "button") located outside the body near the surface of the skin. In one embodiment, the button is equipped with wireless communication capabilities.

Shown in FIGS. 19 and 19a is a scaled conceptual model of PAD at the skin surface of a user. The remaining images schematically show possible functions of the electronics "button" along with several communication paradigms, including: signals stored in memory 262 on the button 260, signals processed 264 on button 260, signals transmitted wirelessly 266 from button 260, and signals processed 268 on the button 260, where said processing leads to a command that is transmitted wirelessly to an endpoint. These functions are described in further detail below:

1. Digitized signals stored in memory on the button. Applications of this embodiment include long-term data recording with intermittent collection and analysis;
2. Digitized signals processed on the button. Processing can include filtering, band-limiting, modeling, etc.;
3. Signals transmitted wirelessly from the button. Transmission protocols can include both short-range (e.g. Bluetooth®, RF) and long-range (e.g. WiFi®) approaches. This embodiment also covers the networking of several buttons, where information from one button may or may not affect processing on another; and
4. On-button processing leads to a command that is transmitted wirelessly to an endpoint. Examples of potential endpoints include (but are not limited to) a motorized prosthesis, a motorized orthosis, a motorized exoskeleton, and a module for functional stimulation of muscle tissue, such as an optogenetic stimulator or a functional electrical stimulation module.

As a further embodiment of this invention, a percutaneous osseointegrated implant can be employed as the PAD through which wires travel. This embodiment of the invention can be combined with embodiments 1-3, described above.

Embodiment 5: System for Closed-Loop Functional Stimulation

In this embodiment, functionality is restored in biological systems that have suffered from impairment of neurological control systems by a closed-loop functional stimulation (CFS) architecture of the invention that is capable of artificially supplementing or replacing damaged neural pathways of paralyzed or weakened musculature.

Another application of the CFS system of the invention is closed-loop control of muscle contraction in a linked residual muscle or regenerative peripheral nerve interface (RPNI) architecture in an amputee. These RPNI models of the invention are architectures that provide 1) efferent motor agonist/antagonist signals for the control of external prosthetic motors, and 2) proprioception and cutaneous afferent feedback into peripheral nerves from external prosthetic sensory signals. The RPNI model of the closed-loop functional stimulation system of the claimed invention utilizes native tissue mechanoreceptors to translate prosthetic sensory information related to muscle stretch and tension, as well as skin pressure and shear, into neural signals similar to those experienced in the normal biological milieu. In contrast to alternative approaches to afferent feedback that bypass native biological tissues, RPNI models of the invention incorporate the specialized biomechanical structures inherently present in muscle and skin to transduce information regarding muscle fascicle state and force, as well as skin mechanoreceptor strain. In utilizing biological structures in the design of these systems, when integrated with current state-of-the-art bionic limb prostheses, amputees experience proprioceptive and cutaneous sensory feedback that approximates or equals that of their previously uninjured state while simultaneously providing a safe and viable peripheral neural interface.

The closed-loop functional stimulation system of the invention can extend the functionality of traditional RPNIs such as those previously described by the seminal work of Cederna et al [15].

The fundamental motor unit to control a biological joint is an agonist-antagonist muscle-tendon pair. Such a muscle-tendon relationship allows organisms to simultaneously control joint state (position and speed) and impedance (stiffness and damping) for upper and lower extremity motor tasks. At least one pair of antagonistic muscles is needed for each degree of freedom of a limb in order to control both joint state, torque and impedance. Although only one Pro-m-RPNI is described per prosthetic degree of freedom, it should be understood by those of ordinary skill in the art that a plurality of Pro-m-RPNI devices could be employed in the control of each degree of freedom of a prosthetic, orthotic or exoskeletal limb.

A major input to joint state afferent sensory information derives from the muscle spindle receptors which are known to discharge when a muscle is passively elongated, but which stop firing abruptly whenever that muscle is slackened passively [17]. When a muscle undergoes an active contraction, however, the discharges from spindle receptors within that muscle could halt or be modified, depending on any activation of spindle intrafusal muscle fibers via Gamma motor neurons [18].

As described above, when a muscle on one side of a biological joint contracts (e.g. muscle A) and moves the joint, this motion elongates the muscle (B) that is attached to the opposite side of the joint and causes the muscle B spindle receptors to discharge. Similarly, if contraction of muscle B causes the joint to rotate towards the opposite direction, then muscle A will be elongated causing the muscle A spindle receptors to discharge. Presumably, the arithmetic difference between the activity levels of muscle A and muscle B spindle afferents would be representative of the "joint" position. This "push-pull" system that exists on each side of a joint in normal physiology can be mimicked when transferring muscles by placing them in opposition to each other using some kind of mechanical system that couples their movements to each other. This construct is herein referred to as a Proprioceptive Muscle RPNI ("Pro-m-RPNI")

In the Pro-m-RPNI construct, electrodes are placed over each muscle of the agonist-antagonist pair. Such electrodes can apply functional electrical stimulation (FES) for prosthetic force feedback from an external prosthesis; by applying FES on the antagonist as the agonist contracts, the force on the agonist can be controlled by the external prosthetic processors based upon synthetic force sensory information from the corresponding prosthetic joint. For example, when an upper extremity prosthetic user picks up a bar bell weight and flexes her prosthetic wrist, the Pro-m-RPNI corresponding to wrist flexors/extensors can be electrically stimulated so the user can experience the barbell weight; as the Pro-m-RPNI agonist muscle contracts, with a motor nerve supply that once innervated the wrist flexors prior to limb amputation, an FES control can be applied to the Pro-m-RPNI antagonist muscle, increasing the force borne by the agonist. The magnitude of the FES stimulation signal would be proportional to the estimated force that would have been applied by the wrist flexors against the bar bell load prior to limb amputation.

Alternatively, FES control applied by the external bionic limb controller can exert a position control on the agonist/antagonist muscles of the Pro-m-RPNI by closing the loop using measured fascicle states. In the case where an external agent is positioning the external bionic joint, such positions would have to be reflected on the agonist/antagonist muscles in order for the prosthetic user to receive accurate proprioceptive feedback. For example, if another person grasps the bionic hand of the prosthetic user with their hand in order to shake the hand of the prosthetic user, such a handshake may forcibly change the positions of the bionic joints. Bionic joint state sensory information would serve as control position and speed targets for a FES control applied to the Pro-m-RPNI muscles by microprocessors positioned on the bionic limb. For example, if the handshake flexed the bionic wrist, the FES controller would receive bionic wrist state information from a synthetic wrist sensor, and apply an electrical activation to the agonist Pro-m-RPNI muscle proportional to the error between the measured bionic wrist position/speed and the measured position/speed from muscle fiber state sensors, causing the muscle to contract and the antagonist to stretch. The prosthetic user would then experience the position of their bionic wrist as imposed by the handshake through afferent feedback to the spinal cord from muscle spindle receptors in the agonist/antagonist pair.

Embodiments of the CFS Architecture of the Invention

Fascicle State Sensing

Robust measurement of muscle fascicle state, including both length and velocity, is important to a closed-loop control architecture for skeletal muscle. Muscle force production is dependent, at least in part, on fascicle length and velocity, and accurate modeling of muscle function generally requires real-time measurements of these parameters. To collect fascicle state measurements, the closed-loop functional stimulation system of the invention optionally includes at least one of the following:

1. Sonomicrometry crystals implanted in the muscle. Absolute distance can be measured in vivo using piezoelectric crystals implanted along muscle fascicles. An "emitter" crystal is stimulated, sending an acoustic pulse through the muscle. After traveling through the muscle, this pulse causes vibration in a "receiver" crystal, which generates a voltage in response to motion. Acoustic signal propagation time through the muscle, the acoustic properties of which are well documented, gives an accurate dynamic representation of fascicle state. Sonomicrometer crystals can be stitched into muscle fibers [19]. Sonomicrometry has been used successfully to measure skeletal muscle length changes in situ and during walking in cats [19] and running in turkeys [20].

2. Ultrasound-indicated surgical sutures visualized using portable ultrasound. Ultrasound has long been viewed as the standard in measurement of muscle fascicle state in humans. Current approaches generally are not able to match the precision of sonomicrometric measurements, but this limitation can be overcome by using ultrasound-indicated surgical sutures to tag and track specific muscle fascicles. In this embodiment, a portable ultrasound probe is incorporated in the CFS of the invention.

3. Ultrasound-based estimation of fascicle length and velocity visualized using portable ultrasound and image processing. With on-line image processing approaches, portable ultrasound can be used for direct estimation of muscle fascicle length and velocity. In this embodiment, a portable ultrasound probe is incorporated in the CFS of the invention, and ultrasound images are processed in real time to provide estimates of fascicle length and velocity.

4. Implantable Myoelectric Sensors (IMES) estimate of fascicle state. IMES technology is expected to have the added capability of fascicle state estimation. The IMES technology, as developed by the Alfred Mann Foundation, for example, measures muscle electromyography and communicates such sensory information wirelessly using an RF link to any external prosthesis, orthosis or exoskeleton. For example, sonomicrometry crystals could be inherent to the IMES design. If two IMES devices are implanted into a muscle, the distance between the IMES could be determined as a measure of muscle state.

Force Sensing

Closed-loop control of skeletal muscle such as by employing the closed-loop functional stimulation system of the invention, generally requires consistent, real-time access to a measurement, or estimation, of muscle force production. To measure or estimate force, any combination of the following approaches can be employed:

1. Neuromuscular-model-based transformation from measured fascicle state and electromyography to force estimate. Models of muscle function are able to predict muscle force from electromyography and some measure of fascicle state [21-22]. Electromyography can be measured either through wired epimysial electrodes or wireless intramuscular electrodes. The electromyographic signal can then be used to estimate muscle activation through a model of activation dynamics, which describe propagation of electrical signal throughout the muscle and subsequent temporal properties of muscle contraction, primarily related to calcium release dynamics in the individual motor units. Activation then serves as the input to a fascicle length and contraction-velocity dependent model of force production. If these parameters are measured directly, as described above, the fully characterized model provides an accurate real-time estimate of force production. Such a force estimate can be employed as a feedback signal in an embodiment of the CFS of the invention.

2. Direct measurement of muscle force through implantable strain gauges. Examples include tendon buckles, which are used as part of standard practice to measure tendon tension in animals, and direct measurement from a strain gauge placed on tendon tissue, which relies on an accurate model of a tendon as a non-linear spring with predictable stress-strain relationships. Both of these approaches currently involve invasive surgery for implantation.

3. Neuromuscular-model-based transformation from measured joint angle and electromyography to force estimate, based on a model of muscle function obtained through metabolic-cost optimization (paralysis model). In the absence of direct fascicle state measurement, metabolic cost optimization can be used to create a model of muscle function that depends on measured joint angle. In this modeling approach, electromyography, joint kinematics, and kinetics are collected for a height/weight matched individual ambulating at a metabolically-optimal walking speed. An optimization approach is then used to define the model parameters that cannot be explicitly measured, where the cost functions are metabolic cost of transport and predicted torque error. Muscle moment arms and trajectories are estimated from scaled musculoskeletal models, allowing an estimate of the relationship between joint position and length of the muscle-tendon complex. Tendons are modeled as non-linear springs, and the optimization procedure selects for metabolically favorable tendon slack lengths and tensile properties. This allows for the generation of a fully-parameterized transformation from joint space to fascicle state for each muscle. With this transformation defined, an external position sensor that measures joint position can serve as the fascicle state feedback necessary to close the loop on muscle force production.

External Sensors

In both the paralysis and RPNI models of CFS of the invention, sensing is not limited to implanted components within the muscle tissue. External sensors can also contribute to CFS function of the system of the invention. Additional sensing components of the CFS system of the invention can include:

1. "Cutaneous" sensors or pressure transducers. These transducers can sense change in displacement, pressure, or other aspects of the external environment, and in turn will send a signal that can be used as an input to either the muscle control paradigm or for cutaneous sensation into the innervating nerve.

2. Joint position sensors placed on the external surface of the joint. As described above, a real-time measurement of joint space can inform model behavior in the absence of direct fascicle state measurements. Additionally, joint position sensors can enable a position based controller, where the feedback loop is closed around position in joint space.

Stimulation

Feedback from the sensing modalities described above drives functional stimulation of implanted or native muscle or muscles. To modulate muscle force production through stimulation, the following approaches can be employed in the closed loop functional stimulation system of the invention:

1. Optogenetic stimulation of opsin-tagged motor neurons, delivered through specially-designed optical cuffs. The neural cell bodies are genetically transfected with genetic material that codes for a light-sensitive opsin. The transfection can occur through a viral vector or other suitable means, such as are known in the art. The cell body of the electrically-excitable cell, which can be a neuron located in the ventral horn, dorsal horn, dorsal root ganglia, or in the muscle cells themselves, will transcribe and translate the light-sensitive protein (opsin), which will embed itself in the cell membrane throughout the axon. This approach was chosen because it may correct both reverse-order motor unit recruitment (defined as the stimulation of easily fatigable fast twitch muscle fibers before the less fatigable slow twitch), and stimulation of non-alpha motor nerve fibers, which are two established issues associated with traditional functional electrical stimulation (FES).

2. Non-invasive, transdermal optogenetic stimulation of opsin-tagged motor neurons. Optogenetics is a relatively new method of genetically transferring light sensitivity to cells in living tissue; typically it has been applied in neurons in vivo, but recent studies demonstrate its effectiveness in skeletal and cardiac myocytes, as well as peripheral/spinal cord neurons. The technique involves genetic modification of host cells to express a light-sensitive ion channel within the cellular membrane. When stimulated with a specific wavelength of light, these channel proteins deform, allowing the passage of ions into the cell; in neurons, this can elicit a depolarization cascade that causes the neuron to fire an action potential. Benefits of optogenetic stimulation over traditional electrical simulation for peripheral nerve control include: genetic specificity, correction of the reverse-order motor unit recruitment problem, neural silencing capability, afferent vs. efferent specificity, and the possibility of simultaneous electrical recording without stimulation artifacts. At this time, there does not exist a method for targeted, non-invasive control of peripheral nerve activity. Such a technology would be of great benefit both in basic and applied neuroscience, as well as a diverse range of peripheral-nerve dependent fields including cardiology, biomechanics, pulmonology, and urology. The closed loop functional stimulation system of the invention employs, in one embodiment, a method that leverages recent discovery of a microbial opsin with radically different optical response characteristics (i.e. having a far red-shifted excitation spectrum) and advances in optogenetic-mediated peripheral nerve stimulation, enabling non-invasive optogenetic stimulation of peripheral nerves. Transdermal illumination enables targeted, non-invasive optogenetic control of peripheral nerves.

One application of this approach under the CFS system of the invention that extends beyond control of skeletal muscle to stimulation of the vagus nerve. The vagus nerve, a peripheral cranial nerve, has been implicated in numerous ailments, including: epilepsy, migraine headaches, obesity, hypertension, fibromyalgia, inflammatory problems such as Crohn's disease, asthma, psychiatric ailments such as depression and obsessive-compulsive disorder. As such, by employing the system and method of the invention, the vagus nerve can be stimulated efficiently with minimal side-effects and potentially high target specificity, benefiting the treatment of various illnesses and disabilities.

3. FES delivered through implanted epimysial electrodes. Electrodes on the epimysium have proven robust in long-term human studies [23] Targeted electrical pulses can be used to modulate force production in the targeted muscle.

4. FES through wireless intramuscular electrodes. BIONs, for example, can be used to deliver targeted functional electrical stimulation.

5. FES delivered through implanted neural cuff electrodes. Neural cuffs can be used to deliver targeted functional electrical stimulation along the biologically relevant pathways, although this approach may be compromised by collateral stimulation of pain receptors in the peripheral nerve bundles.

6. FES delivered through an implanted multi-channel electrode array. Employment of a multi-channel electrode array in the CFS system of the invention can provide for selective motor neuron stimulation and precise control of motor unit activation, enabling control of muscle force production. This embodiment solves the reverse-order recruitment problem, but requires a very high resolution on the array, so that small nerve fibers can be isolated and stimulated separately from large fibers.

Through-Skin Signal Transmission

Through-skin transmission of both signals and power is an integral part of the CFS system of the invention. Herein we describe several methodologies for bidirectional through-skin communications.

1. Long-term viable percutaneous access device (PAD) technology. This architecture is similar to that described in Embodiment 4. Suitable PAD technology provides for direct electrical access to all elements of the CFS architecture of the invention while overcoming the power transmission inefficiency and bit-rate limitation inherent to implanted wireless technologies. One example of such a suitable PAD is the device created by Viaderm, LLC. The Viaderm® tissue-engineered percutaneous access device (ViaDerm1 PAD) [2] is a component of the CardioVAD Left Ventricular Assist Device system (LVAD Technology, Inc) unconditionally approved in 2009 for an FDA IDE Pilot trial [7] in 25 patients in up to 5 clinical centers.

2. Wireless inductive coupling from an immediately-subcutaneous base station. Although power efficiency is relatively poor in inductive applications, inductive communication has demonstrated increased efficiency over short distances. Rather than attempting to use a large RF field to penetrate to deeply-implanted electronic interfaces, an intermediary communication port can be employed. In this embodiment, a passive "base station" containing an RF antenna is wired to each of the implanted elements of the CFS system of the invention, and placed immediately below the surface of the skin. An inductive transmission coil is placed on the external surface of the skin. Signals and power are transmitted inductively through the skin over a relatively short distance.

3. Wireless inductive coupling from deep-muscle transmitters built on or near the implants. In this embodiment, the passive "base station" describe above is replaced with smaller transmitters, localized to the affected muscle. These transmitters may be stand-alone units, or may be built directly into the implanted elements of the CFS system. For example, the transmitter can be embedded directly into an epimysial electrode. Although this embodiment would suffer the efficiency losses inherent to inductive power transmission at distance, it significantly reduces the internal wiring necessary to connect each implanted device to a single base station.

Control Architecture (Paralysis Model)

In the paralysis model, the CFS system of the invention stimulates muscle tissue to replicate the behavior of healthy biological muscle, as if that muscle were fully integrated with the peripheral and central nervous system. Accurate models of biological muscle function and control enable the CFS system of the invention to calculate appropriate biologically-relevant target joint torques, and the closed-loop feedback inherent to the CFS system of the invention ensures that those torques are produced. The following control approaches are suitable for use with the CFS system of the invention:

1. Spino-reflexive neuromuscular model Involuntary neural reflex pathways play a central role in gait. It has been demonstrated, using forward dynamic models of human locomotion, that simple spino-reflex architectures in lower-extremity musculature are sufficient to generate normalized gait. In this embodiment, the processing unit serves as an artificial spinal cord, using force and state information as inputs to modeled reflex arcs, which generate stimulation paradigms that cause muscle contraction and produce forces.

2. Gain modulated spino-reflexive model. In cases where limited neural input is available, the reflex arcs described in the spino-reflexive neuromuscular model are modified to allow neural modulation of reflex gains. It is hypothesized that this system will facilitate gait adaptation by retaining volitional input of the joint torque produced by the CFS system.

3. Neuromuscular-model-based volitional control. Several neuromuscular pathologies come as a result of damaged communication pathways. If a neural recording unit were placed upstream of the damage pathway, either in the peripheral nerve trunk or in the central nervous system, the CFS system of the invention could be used to bridge the gap caused by the damaged neural tissue. In this embodiment, neural information is communicated to the processing unit, which then uses a neuromuscular model to interpret user intent, and generate muscle contraction that matches intent.

Cutaneous Sensory Feedback (Amputation Model)

The CFS system of the invention integrates with an architecture to provide cutaneous sensory feedback to the subject. Although not an exhaustive list of the possible embodiments, two suitable methods of preparing cutaneous nerves to provide feedback are listed below.

1. Transmigration of one-or-multiple innervated skin patches from the amputated limb to the residuum. One-or-multiple innervated skin patches, distal to the transfection line, are preserved during the amputation. A neurovascular island is created, as both the nerve and vascular supply to the skin patch remain intact. The neurovascular islands are then incorporated into the surface of the residuum. Because the native nerve supply is retained and remains viable, manipulation of the cutaneous tissue or the associated nerve is perceived as originating from the pre-amputation skin location.

2. Reinnervation of one-or-multiple residual skin patches. One-or-multiple transected nerves from the amputated limb are held in proximity to one-or-multiple skin patches in the residuum, until reinnervation occurs. This is expected to have similar effects on sensory perception to full transmigration of a neurovascular island. However, this approach necessitates the deinnervation of cutaneous tissue in the residual skin patch that is to be reinnervated, to make room for the transected nerves from the amputated limb.

Once a viable, innervated skin patch has been prepared (either by one of the methods above or by another method), any combination of the following approaches can be employed to provide cutaneous sensory feedback:

1. Mechanical manipulation of the skin patch by an external device. An electro-mechanical device outside the body manipulates the skin patch to simulate a variety of sensations. For example, a series of indenters simulate distinct pressure patterns, while a sliding block simulates shear. This approach recreates for the user, with very high fidelity, any sensation that can be replicated by small mechanical actuators.

2. Electrical stimulation of the associated afferent nerve by a nerve cuff. Temporal and spatial modulation of stimulation patterns on a cuff electrode has been shown to restore graded touch perception in an amputee. [24].

3. Electrical stimulation of the associated afferent nerve by a microchannel array. This technique is only viable as a part of a reinnervation paradigm (see reinnervation method above). A microchannel array is placed between the distal end of the transected nerve and the deinnervated skin patch. Once the nerve regenerates through the array and into the skin patch, the array can be used both to record afferent neural activity in the skin, and to simulate a variety of sensations.

4. Optogenetic stimulation of the associated afferent nerve by optical cuffs. One method to provide cutaneous sensory feedback involves transfecting only the cutaneous fibers with genetic material coding for a light-sensitive protein that can open ion channels in the axon membrane eliciting a depolarization action potential in response to light input matching the opsin's spectral profile. Selective targeting of cutaneous fibers can be achieved through several means including unique location of the injection site within the target tissue, selection of any number of genetic promoters in combination with opsin to control protein expression in target neuron, use of viral vectors that are specific for sensory neurons via serotype analysis, input signal modulation of light delivery, directed targeting from independently controlled light sources on optical cuff itself or another method not here described. Sensory feedback is not limited to cutaneous feedback via the mechanoreceptors in the skin. Sensory feedback can also include proprioceptive feedback via selective targeting of afferent nerves within the intrafusal muscle bundles (Ia and II afferents) or other sensory autonomics (e.g., vascular tone). A novel optical nerve cuff 300 using microLEDs 302 is shown in FIGS. 20A-20F. Optical cuff 300 can employ microLEDs 302 and may have electronics embedded within it, such as electronic microcontroller 304, used to control the LEDs or to power an electrical interface also located on the interior surface of the cuff. Wire 306 connects microLEDs 302 and, additionally, other components of cuff 300 to a power source, not shown. Typically optical cuff 300 is formed of a suitable material known to those skilled in the art, such as biocompatible silicone 301. Individual LEDs 302 can be independently controlled or not. The optical cuff can present a method for providing either proprioceptive or cutaneous feedback to a nerve that has an opsin protein embedded within the membrane of the nerve. In addition, the optical cuff can be used for FES of muscle by stimulating the innervating nerve. The opsin protein may include channelrhodopsin, halorhodopsin or another opsin derived from a living organism (e.g., bacteria) or synthetically produced in a laboratory environment.

Clinical Examples

Figures 21A, 21B, 21C:
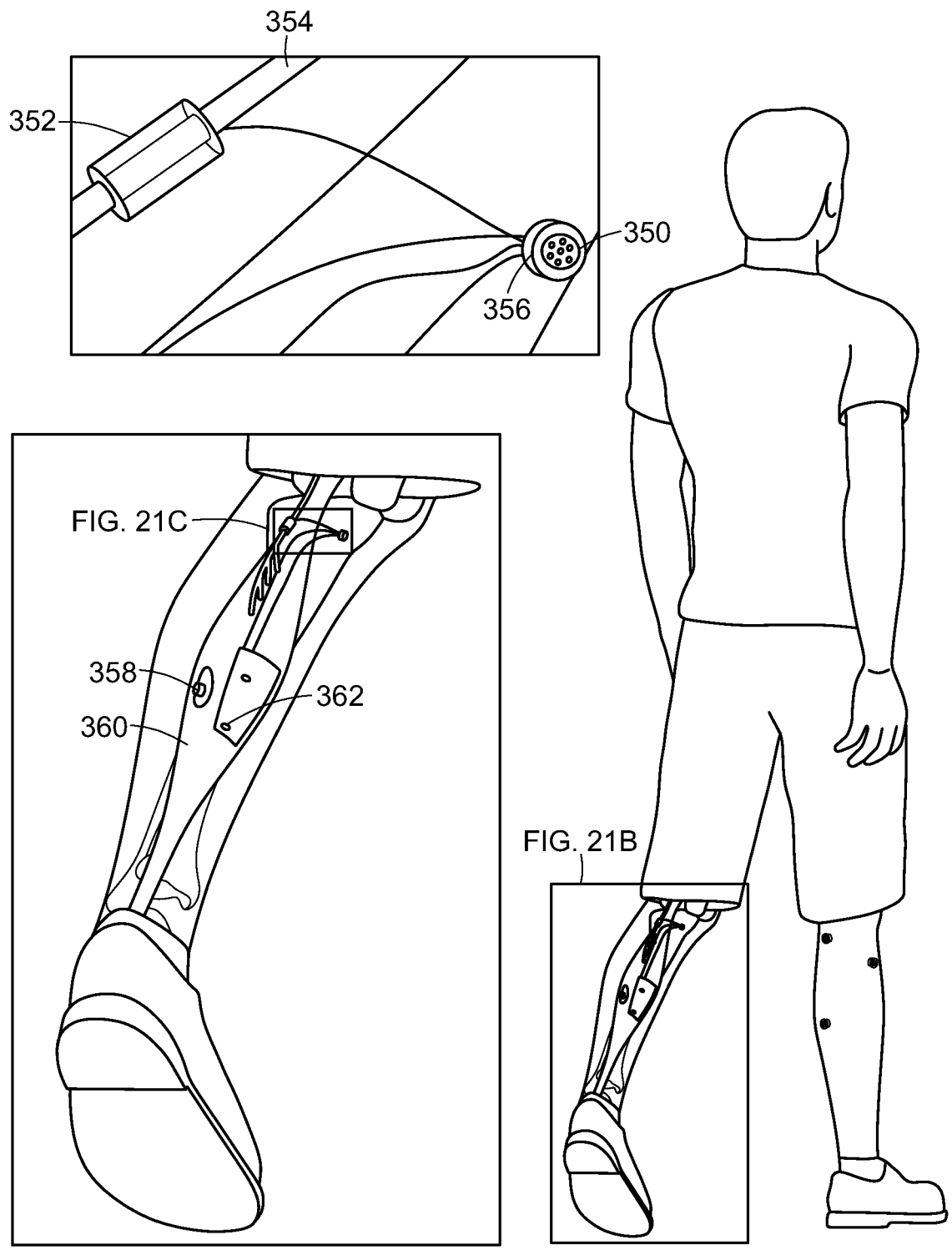
FIGS. 21A-C are three-dimensional representations of a system of the fifth embodiment of the invention, wherein the system has been implanted in a subject.

One example of a clinical application of the CFS technology of the invention includes treating a paralyzed or weakened calf muscle by employing a system 350 of a method of this embodiment of the invention, such as is shown in FIGS. 21A-C, which includes: optical or neural cuff 352 for stimulation; tibial nerve 354, percutaneous access device and electronic button 356; bipolar epimysial electrode for recording 358; gastrocnemius 360; and sonomicrometry crystals 362. Electronic button 356 receives muscle electromyographic, length, and velocity sensory information from electrode 358 and crystals 362. Wires from these passive sensors pass through the skin membrane via the percutaneous access device (button 356). Using a muscle computational model running on a microprocessor unit within the electronic button, such as the Hill muscle model, gastrocnemius muscle force is estimated using the electromyography and state sensory information. The microprocessor controller then outputs an optical/neural signal to actuate the optical or neural nerve via cuff 352.

Figures 22A, 22B:
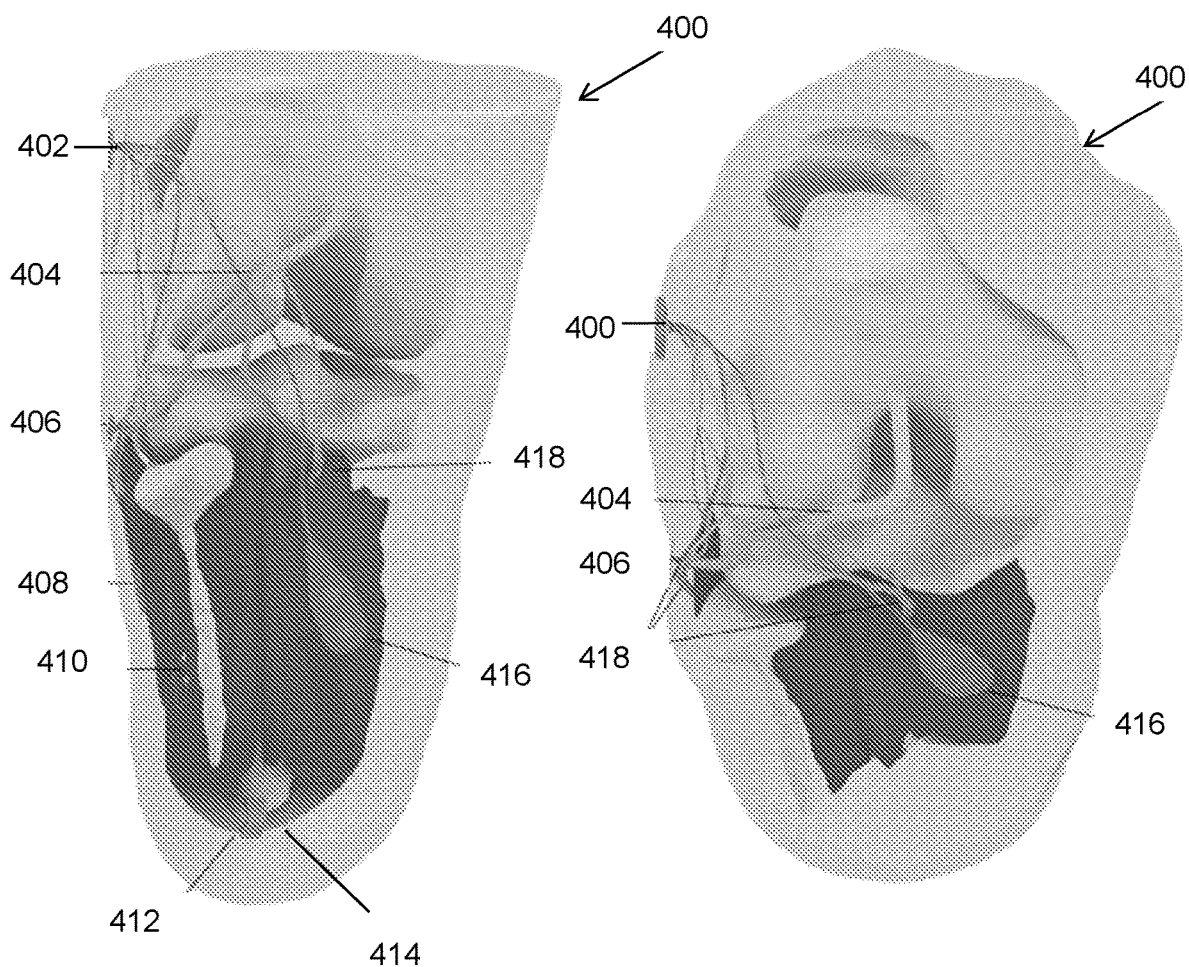
FIG. 22A is a three-dimensional representation of another version of the fifth embodiment of the invention, wherein the system of the invention is located in a trans-tibial amputee, and the agonist/antagonist muscles are mechanically coupled over a surgically-constructed sliding surface, and then instrumented and controlled.
FIG. 22B is another three-dimensional representation of the version of the fifth embodiment of the invention, shown in FIG. 22A shown from another perspective.

In another example of this invention, the CFS transtibial amputee, is combined in subject 400 with the surgical architecture from Embodiment 1, and is shown in FIGS. 22A and 22B. This embodiment includes: percutaneous access device 402, sciatic nerve and downstream branches 404, preserved or reinnervated skin patch 406 for cutaneous feedback; bipolar epimysial electrode 408 for recording from or stimulating an antagonist muscle; sonomicrometry crystals 410, agonist-antagonist pair 412 coupled across a surgically constructed sliding surface 414; bipolar epimysial electrode 416 for recording from or stimulating the agonist muscle; and optical or neural cuff 418 for stimulation.

Figure 23D:
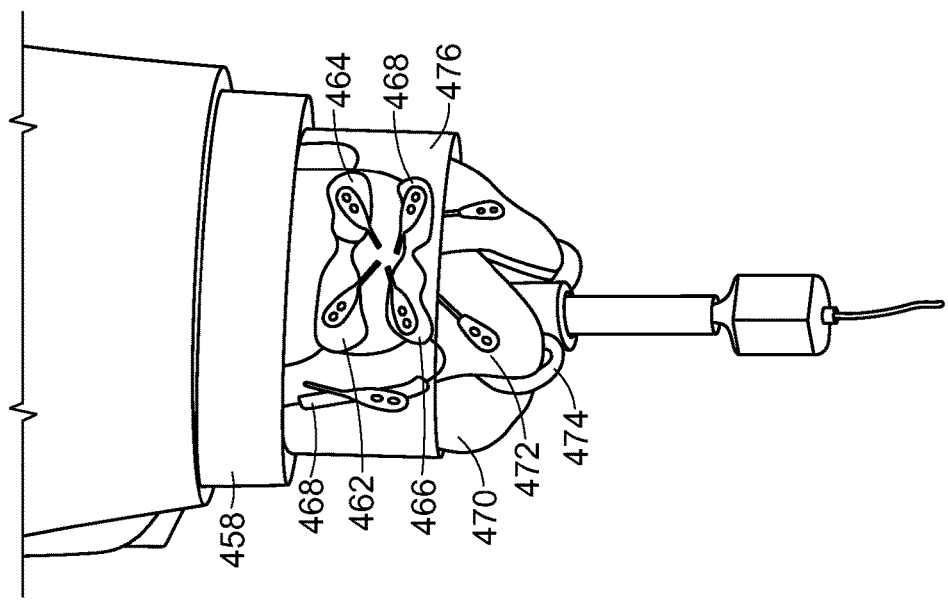
FIG. 23D is a view from still another angle of the three-dimensional representation of the fifth embodiment of the invention shown in FIG. 23A.
Figure 23C:
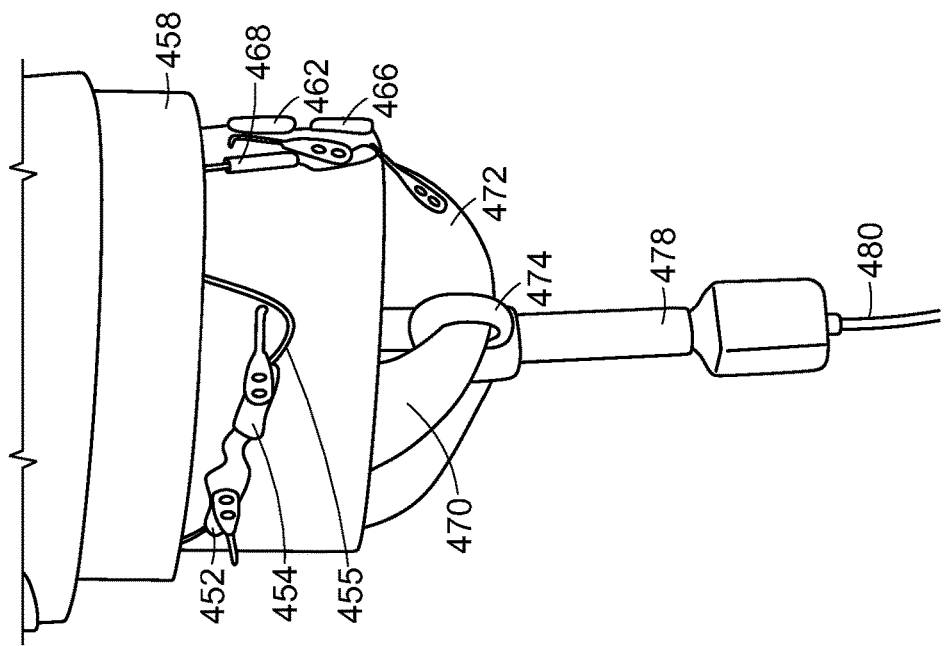
FIG. 23C is a view from another angle of the three-dimensional representation of the fifth embodiment of the invention shown in FIG. 23A
Figure 23A:
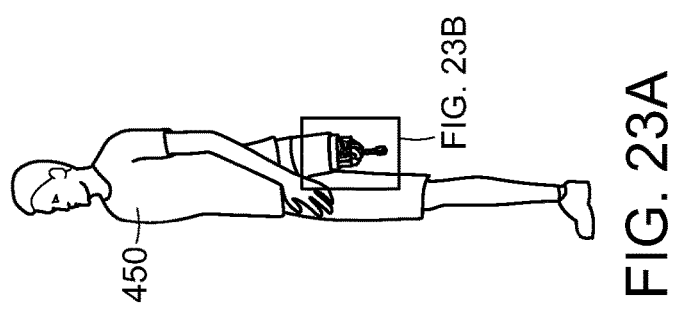
FIG. 23A is a three-dimensional representation of a fifth embodiment of the invention, including a closed-loop functional stimulation (CFS) system in a transfemoral amputee.
Figure 23B:
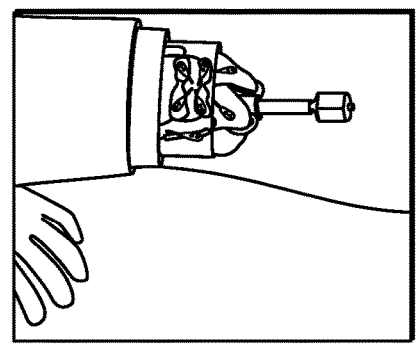
FIG. 23B is a three-dimensional representation of the fifth embodiment of the invention, as a detail of FIG. 23A, viewed from a different angle.

FIGS. 23A, 23B and 23C show an example of a CFS system of the invention in a transfemoral amputation model. In FIGS. 23A and 23B, linear RPNI constructs are anchored at both ends to an external surface of muscle fascia. This approach causes all force produced by either muscle within the linear RPNI construct to be transduced along the entirety of the RPNI construct. For example, in an agonist-antagonist pair with muscles A and B, if muscle A contracts, it will stretch muscle B, causing the spindle fibers in muscle B to fire proportionate to the strain in muscle B. Golgi tendon organs in the musculotendonous junction will also fire, with an intensity proportionate to the force felt at the junction, providing afferent force feedback. CFS of this invention ensures that the proprioception and force feedback are consistent with the position and torque of the prosthetic joint. From FIGS. 23A, 23B and 23C, elements of this example of a transfemoral implementation in subject 450 of CFS include: Metatarsal-Phalangeal (MTP) extensor 452; MTP flexor 454; nerve supply 456; adipose tissue 458; De-epithelialized skin patch 460 from ball of foot; as part of Cut-s-RPNI; ankle extensor 462; ankle flexor 464; subtalar invertor 466; subtalar invertor 468; knee flexors 470; knee extensors 472; tendon loops 474 sutured to periosteum; fascia 476; osseo-neural conduit 478; and wire bundle 480 to external device (not shown).

FIGS. 24-28 are control diagrams that describe how the CFS control paradigms interact with the afferent feedback mechanisms according to various embodiments of the invention. In the first embodiment of the CFS controller, shown in FIG. 24, optogenetic stimulation drives muscle contraction based on an automated reflex arc. Measured EMG (electrodes) and fascicle state (sonomicrometry) are input to a neuromuscular model to estimate muscle force production. Together with fascicle state information, this estimated force will drive a computational reflex model that runs on a microprocessor within the electronic button, by which a deterministic function of muscle force, fascicle length, and fascicle velocity will be used to govern optogenetic stimulation, the output of the microprocessor controller. For example, in the case of the weakened or paralyzed calf muscle application shown in FIG. 21, the computational reflex model would comprise a reflexive function where calf muscle length, speed and force would determine calf muscle activation. The microprocessor controller would then command in real-time the output of optical signals via the optical nerve cuff causing the muscle to contract in a manner comparable to a natural spino-reflexive response.

Figure 24:
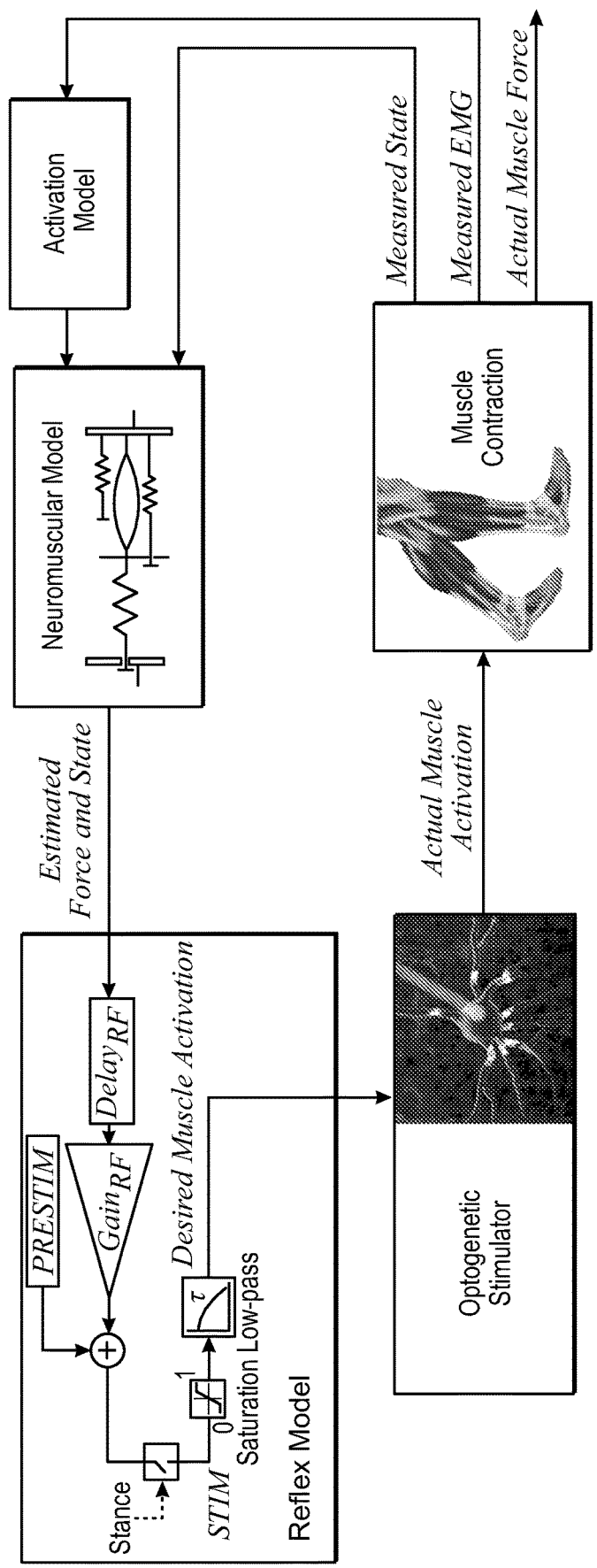
FIG. 24 is a schematic representation of an automated reflex arc controller of a fifth embodiment of the invention.
Figure 25:
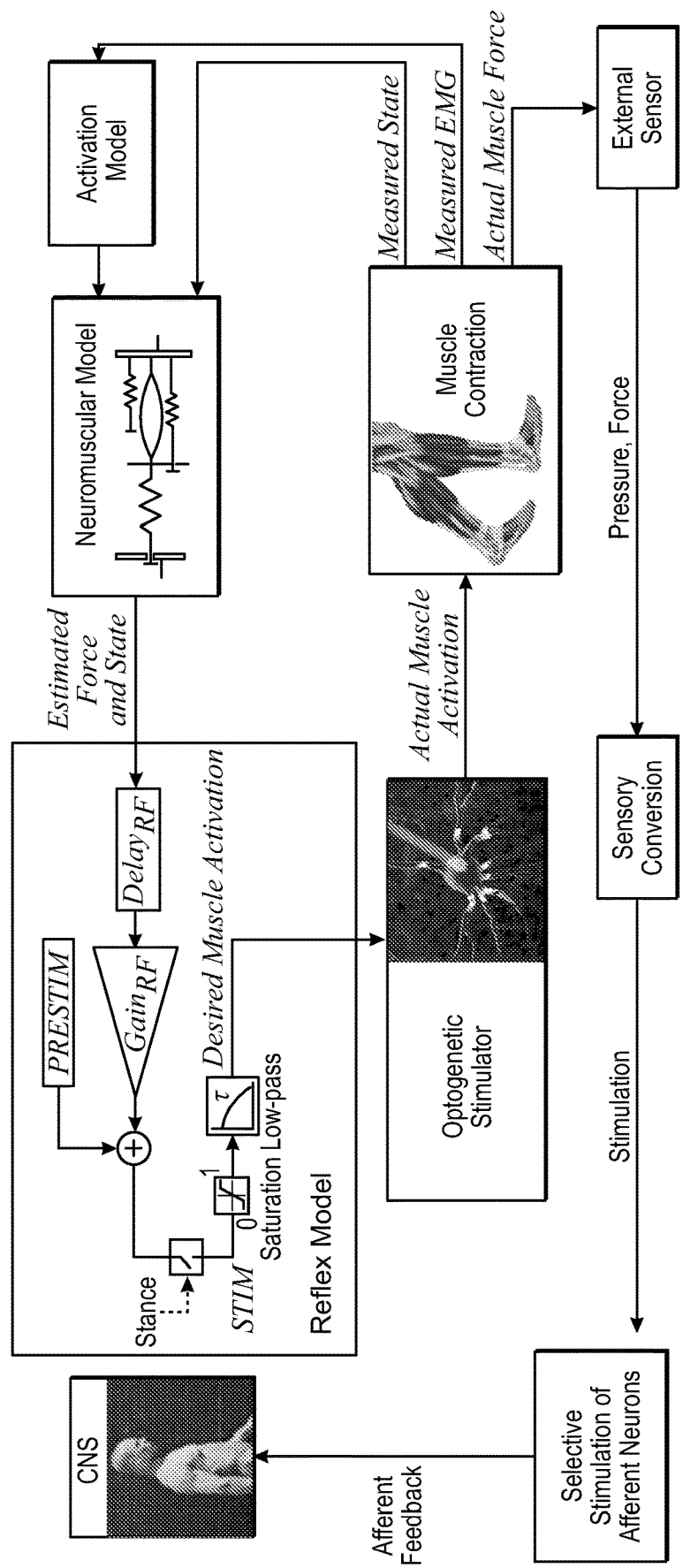
FIG. 25 is a schematic representation of an automated reflex arc controller with afferent feedback of the fifth embodiment of the invention.

FIG. 25 shows the control system of FIG. 24 in the context of an afferent feedback loop, in which information from an external sensor communicates with the patient's nervous system to provide information about the affected limb.

Figure 26:
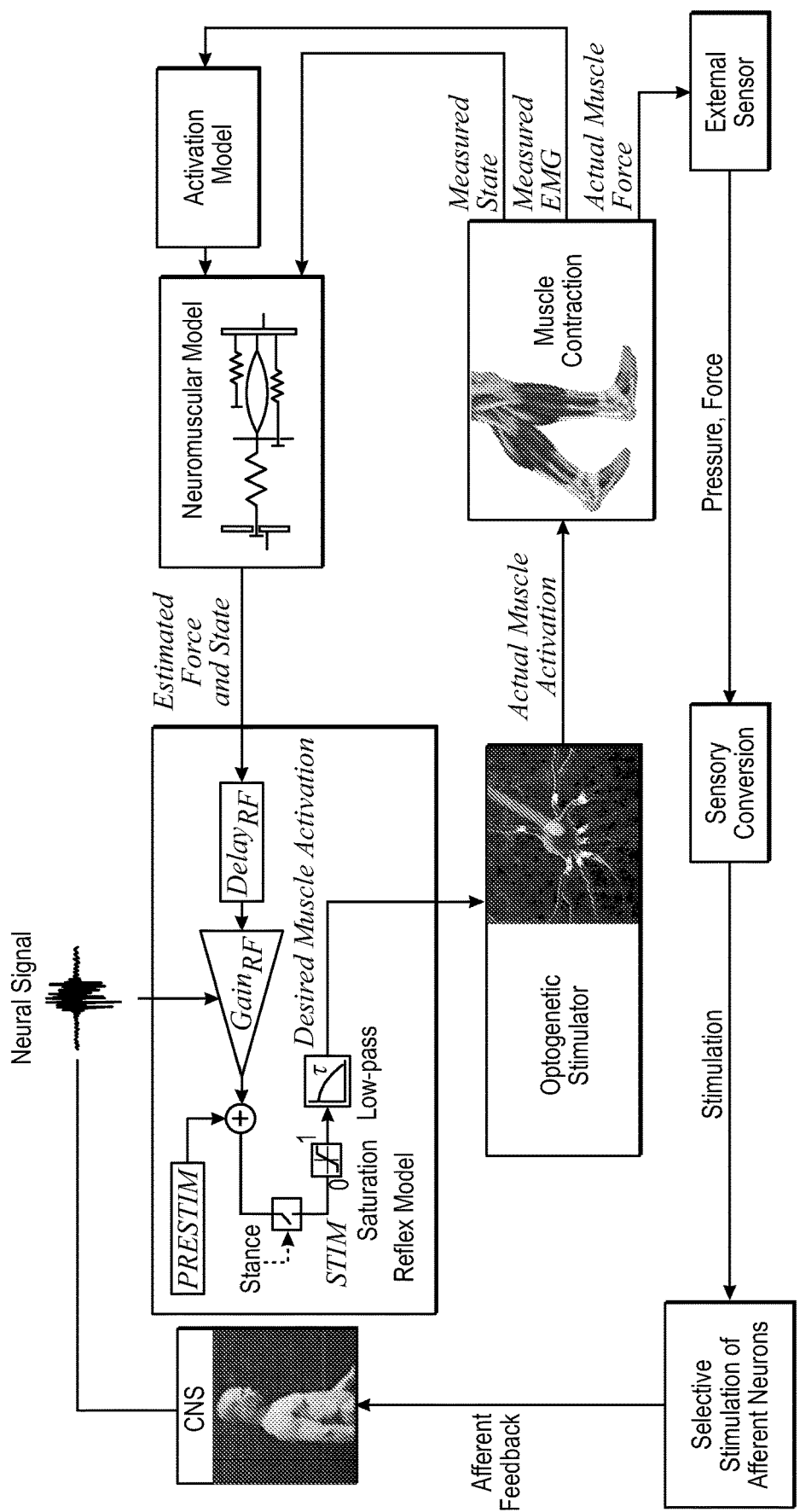
FIG. 26 is a schematic representation of a gain-modulated reflex arc controller with afferent feedback according to another version of the fifth embodiment of the invention.

In another embodiment of the CFS controller employed in one embodiment of the invention, optogenetic stimulation drives muscle contraction based on a gain-modulated reflex arc. The system functions as described in FIG. 25, with the addition of a neurally-modulated reflex gain. This added feature improves patient control of the reflexive stimulation. The system is shown in FIG. 26.

Figure 27:
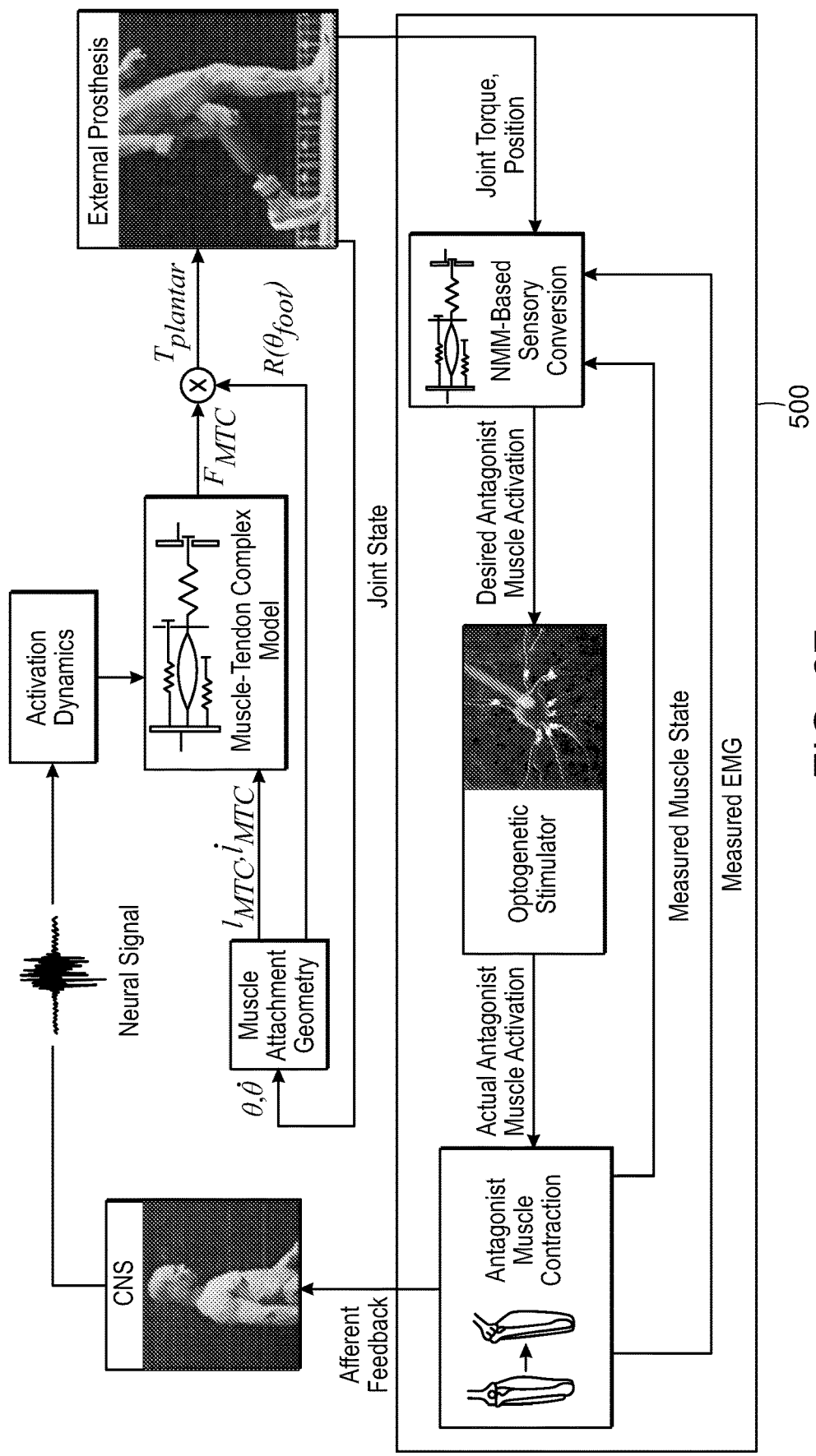
FIG. 27 is a schematic representation of a direct neuro-musculoskeletal model-based controller with afferent feedback, as applied to a prosthesis according to another version of the fifth embodiment the invention. The CFS component of the fifth embodiment of the invention is enclosed in box 500.

FIG. 27 shows how one embodiment of the invention of the CFS fits into the control paradigm of a powered-prosthesis. The CFS component of this embodiment of the invention is enclosed in box 500. Neural signal from the patient drives a computational neuromuscular model running on the microprocessor controller, which determines torque output at the prosthesis. Feedback is then provided by modulating the relative lengths of a coupled agonist-antagonist muscle pair. CFS is used to regulate the contraction of the antagonist muscle to oppose contraction of the agonist muscle. A more detailed description of the roll of CFS in the agonist-antagonist framework of one embodiment of the CFS system of the invention was described previously herein.

Figure 28:
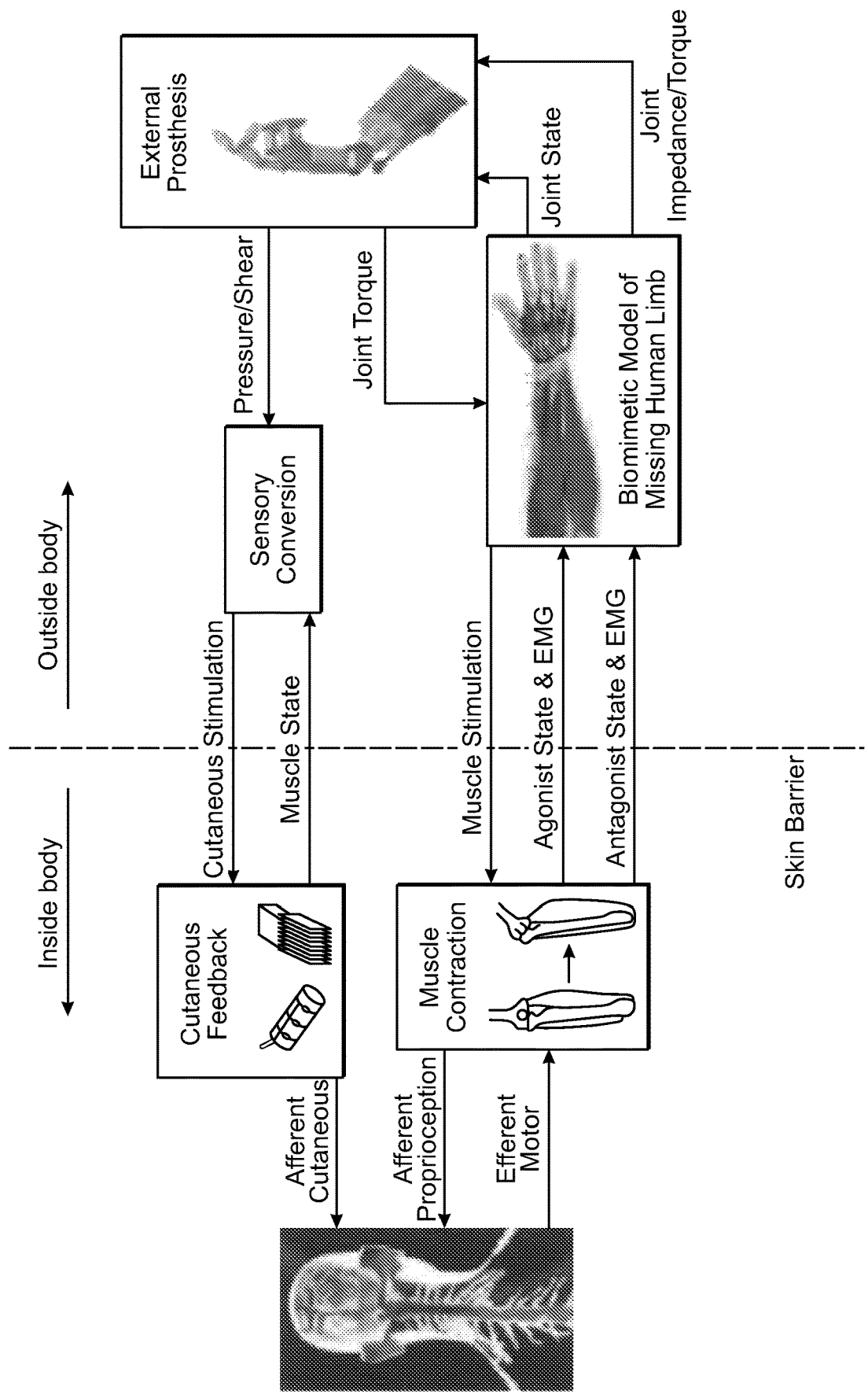
FIG. 28 is a schematic representation of a complete control system for an amputee according to one version of the fifth embodiment of the invention.

FIG. 28 shows one embodiment of the full CFS system of the invention, as applied in an amputee. Closed-loop feedback of muscle contraction is essential to ensure that the stimulation-based feedback provided to the patient is both reliable and repeatable.

Successful implementation of the CFS architecture of the invention depends on a reliable integrated electronics platform. Hereafter we describe the details of one embodiment of this platform.

Figure 29:
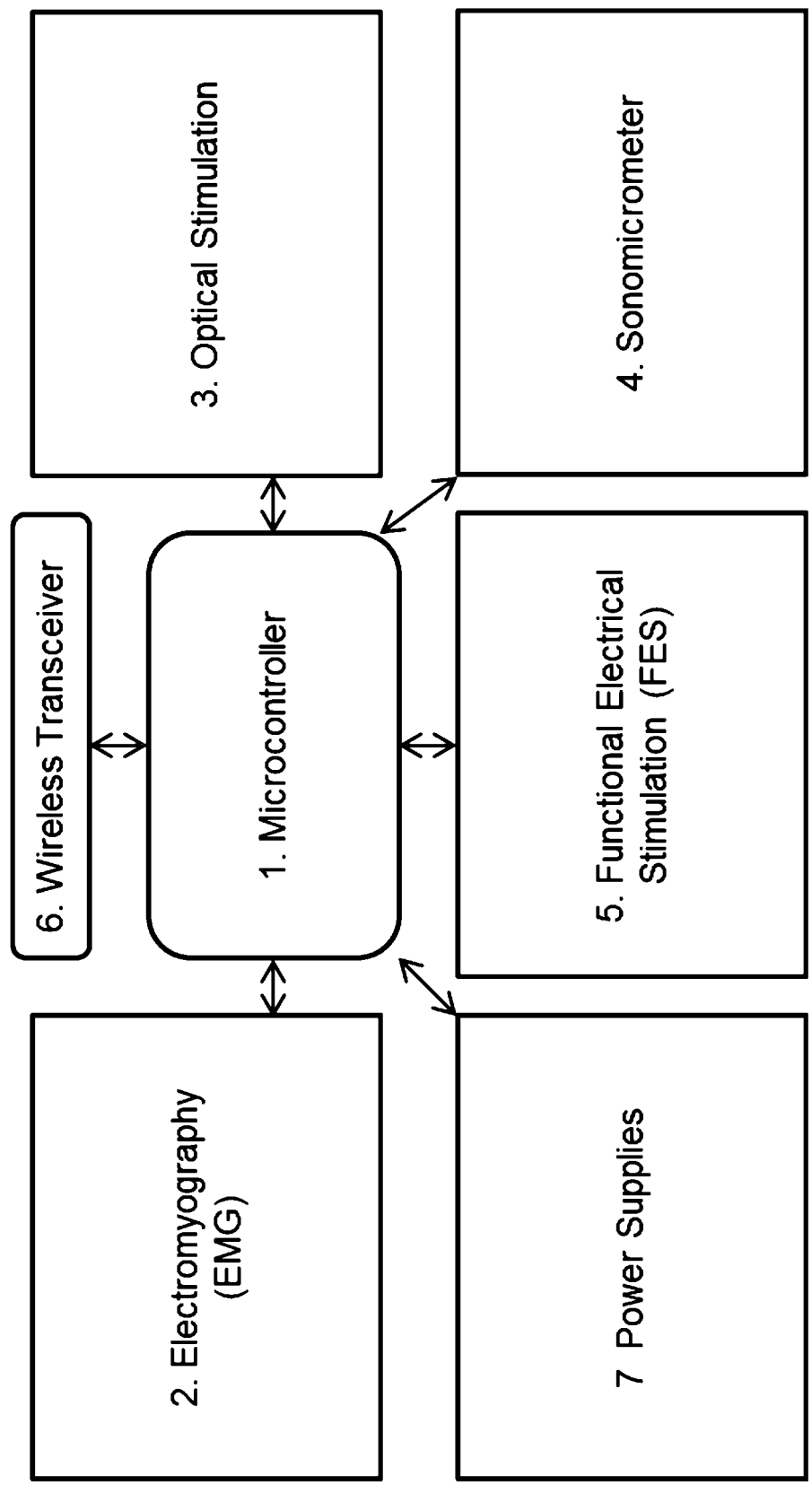
FIG. 29 is a schematic illustration of an example CFS system.

Shown in FIG. 29 is a schematic representation of a CFS electronic architecture of a fifth embodiment of the invention, including a microcontroller (1); an electromyography unit (2); an optical stimulation unit (3); a sonomicrometry unit (4); a functional electrical stimulation (FES) (5); a wireless transceiver (6); and power supplies (7).

Description: A system, such as shown in FIG. 29, can be used to "read and write" from/to muscles and nerves can be used for scientific experiments, as a test instrument, or in-situ applications. The system supports Electromyography (EMG) (measure muscle activation), Optical Stimulation (for optogenetics-based nerve stimulation), Sonomicrometry (to measure muscle length and velocity), and Functional Electrical Stimulation (FES) (to electrically activate muscle fibers). The system can be used for closed-loop control algorithms, can communicate (wired, or wireless) to an external computer, and can be battery operated. A main value of this design comes from the presence of all the different modules in one circuit, allowing algorithms to control outputs based on measured signals in a closed-loop fashion. It will also be small and power efficient, enabling long term field experimentation and use.

1. Microcontroller

Figure 30:
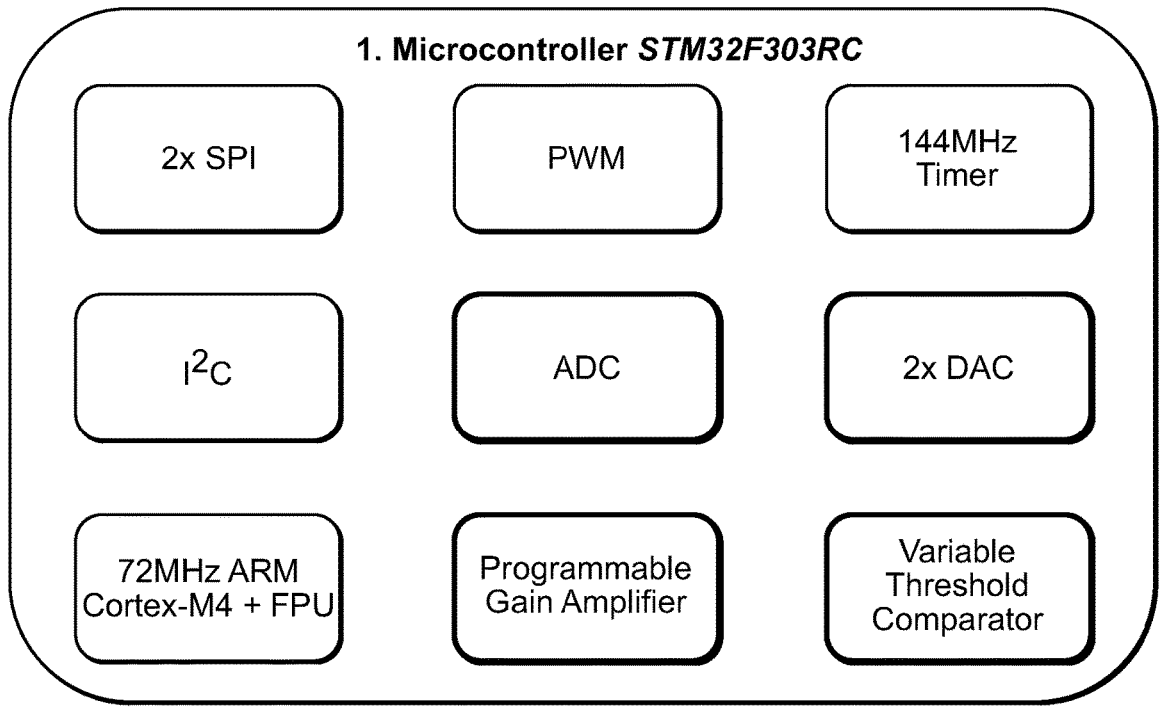
FIG. 30 is a representation of a micro-controller to be employed in the fifth embodiment of the invention.

With reference to FIG. 30: the microcontroller (µC) is used to read data from sensors, control output devices, run algorithms and process data. All the modules except power supplies 7 depend on microcontroller 1 for their operation.

Specific: STM32F303RC, STMicroelectronics, Cortex-M4F

Generic: 8/16/32 bits microcontroller (µC), digital signal processor (DSP), microprocessor (µP) or programmable logic component (CPLD, FPGA). Contains the following peripherals: SPI, PWM, Timers, ADC, DAC, Programmable Gain Amplifiers (PGA), Comparators. The peripherals could be discrete external components.

2. Electromyography (EMG)

Figure 31:
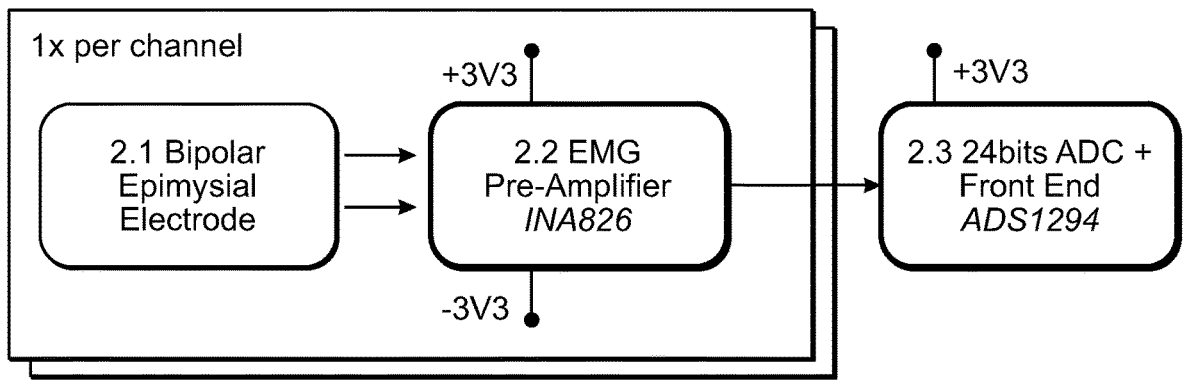
FIG. 31 is a schematic representation of an electromyographic module employed in the fifth embodiment of the invention.

With reference to FIG. 31: one bipolar epimysial electrode (2.1) is used per muscle. A tiny instrumentation amplifier circuit (2.2) is attached to the electrode and provides a differential gain of 25. The resulting signal, unipolar and centered at 1.65V, is sent to the ADS1294 ADC/Biomedical front-end combo (2.3). It can be amplified by a gain of 1, 2, 3, 4, 6, 8 or 12 (combined gain of 25 to 300V/V) before being digitized. The 4 channels can be sampled simultaneously. Each pre-amp requires ±3V3, GND and an output signal (4 wires). Power can be shared, the number of external wires is w=3+n where n is the number of channels.

2.1: While the more generic term 'electrode' is preferable, suitable types of electrodes include unipolar, bipolar, etc. Electrode 2.1 can be the same part as electrode 5.1, or two components can be used.

2.2: the pre-amplifier is based on an instrumentation amplifier integrated circuit (IC). In the example shown, the INA826 is employed, but many other instrumentation amplifier IC's can be used. The gain does not have to be fixed at 25. This circuit can be implanted (glued to the back of Electrode (2.1), near Electrode (2.1)) or external to the body. This stage includes low-pass filters.

2.3: The ADS1294 is an integrated circuit that combines multiple analog to digital converters (ADC) and programmable gain amplifiers (PGA) with an SPI interface. All those modules could be discrete components, or another integrated circuit could be used.

A generic description could be, for example, "Any circuit that can amplify voltage levels in the µV or mV range with enough gain to cover the input span of an analog to digital converter (ADC, any technology or number of bits), and provide enough filtering to discriminate useful information from noise."

3. Optical Stimulation

Figure 32:
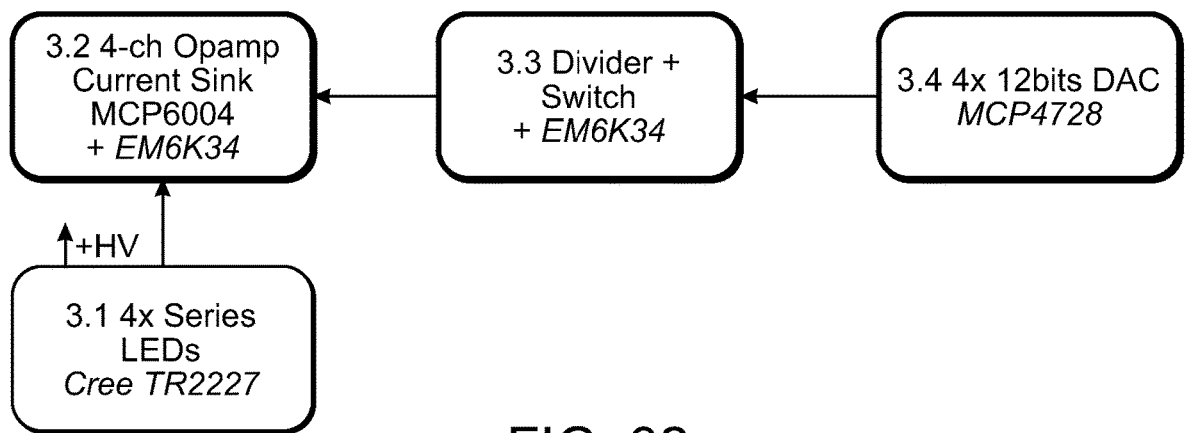
FIG. 32 is a schematic representation of an optical stimulation module of the fifth embodiment of the invention.

With reference to FIG. 32: the LED current is regulated by a linear, opamp based current sink. The µC can control the current magnitude via a DAC, and pulse the outputs via transistor switches. The Boost power supply is programmed (by selecting a resistor value during assembly) to provide just enough voltage for 4, 6 or 8 series LED per string, thus maximizing the efficiency.

3.1: the circuit can support 4, 6 or 8 series LEDs. Any number of series or parallel LEDs (or light emitting devices, for that matter) can be supported.

3.2: linear current sink (or controller) based on an operational amplifier (opamp). Can be a current source or sink, can be an integrated circuit, can be any other circuit topology, as long as we can get a known current when we apply a known voltage input.

3.3: this circuit is used to generate voltage pulses from 0 to 100 mV, of any duration and frequency. Generic description: "voltage pulse generation".

3.4: digital to analog converter (DAC), can be any number of bits, any topology, any digital interface. Used to generate fix voltages that are then used by the pulse generator (3.4). The magnitude of the voltage will determine what current is sent to the LEDs.

4. Sonomicrometer

Figure 33:
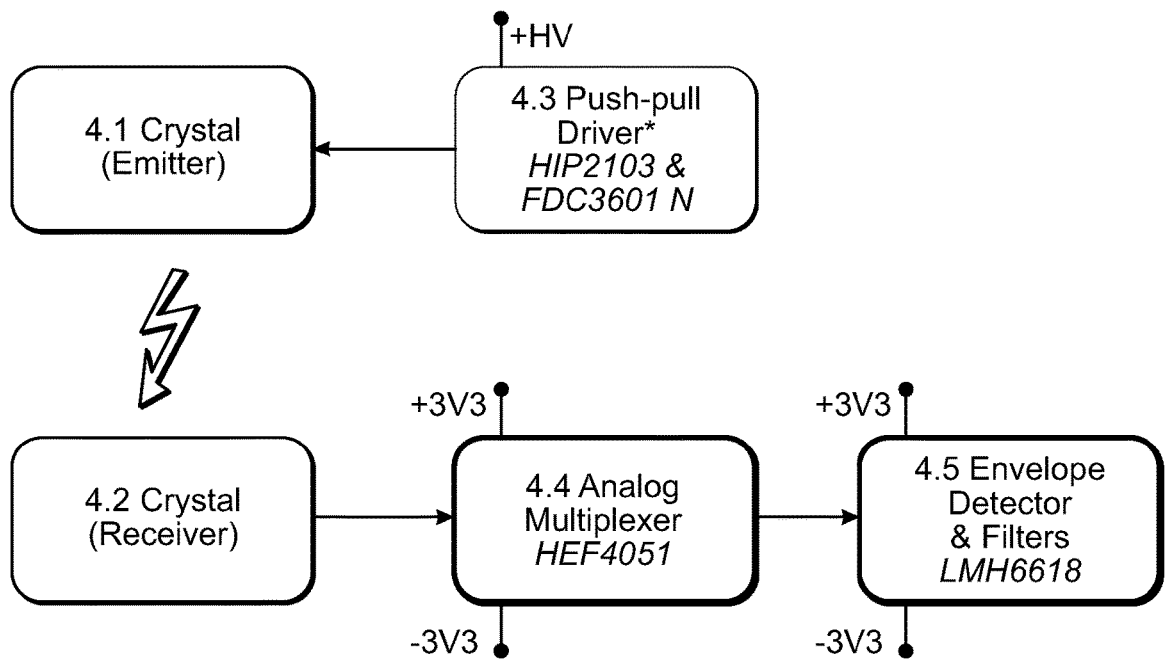
FIG. 33 is a schematic representation of a sonomicrometry module of the fifth embodiment of the invention.

With reference to FIG. 33: the microcontroller emits one pulse per channel every 200 µs (5 kHz). The received waveform goes through a filtered envelope detector and an amplifier. The resulting voltage is sent to an ADC and a comparator. Software is used to find the peak and adjust the amplifier gain and the comparator threshold. No manual calibration is required. A timer measures the time between the emission of the pulse and the comparator's detection to accurately determine the muscle length (down to a few µm).

4.1 & 4.2: piezo crystals, commercial product. Can be of any size, voltage and resonant frequency.

4.3: circuit used to drive the emitter crystal. A push-pull driver is employed (h-bridge) but any circuit topology can be used (low-side switch, high-side switch, full bridge, etc.).

4.4: analog multiplexer that allows the use of one envelope detector/demodulator 4.5 with multiple piezocrystals 4.2. Can be made with discrete components, or with a different IC. Can be unidirectional or bidirectional, unipolar or bipolar.

4.5: envelope detector/demodulator built with an operating amplifier (opamp) and discrete components. Includes low- and high-pass filters.

The 200 μs/5 kHz is a suitable example for use with this invention. Multiple channels can be multiplexed, either interleaved or simultaneously triggered.

One particularity of this module, versus commercial products and published designs, is the reliance on the microcontroller to greatly reduce the number of discrete components required. The auto-calibration is a nice feature to minimize the labor required to operate the device, but it can also increase the precision of the system over-time as the calibration can't "slip."

5. Functional Electrical Stimulation (FES)

Figure 34:
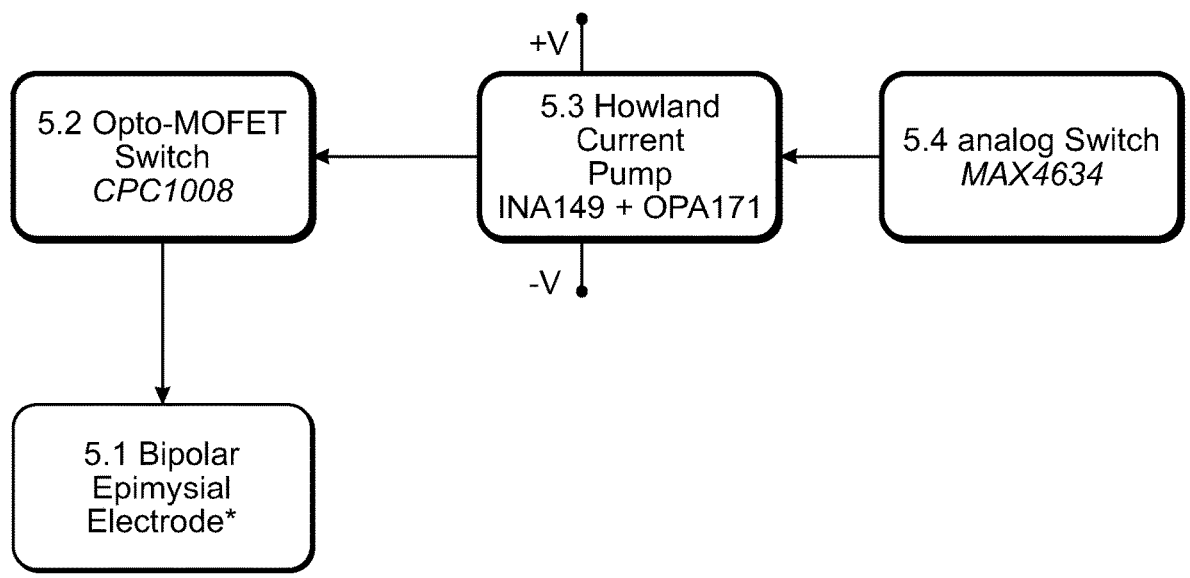
FIG. 34 is a schematic representation of a functional electrical stimulation unit of the fifth embodiment of the invention.

With reference to FIG. 34: the current generated by the Howland Current Pump (HCP) is controlled by the μC (DAC for the amplitude, analog switch for the pulse width and polarity). Opto-MOFFETs solid state switches are used to multiplex the output.

5.1: The more generic term 'electrode' is preferable. Include full list of available types (unipolar, bipolar, etc.). Electrode 5.1 can be the same part as electrode 2.1, or 2 components can be used.

5.2: opto-MOSFETs used to multiplex the output. Any switch topology can be used, as long as it allows multiple electrodes to be used with one current pulse generator.

5.3: bipolar current source, based on the Howland Current Pump circuit. Can be any circuit topology. Can be powered from low-voltages (below 36V) or from high-voltage (up to 300V). Output can be unipolar or bipolar. A voltage controls the output current.

5.4: analog switch used to generate pulses of any voltage, length and frequency. The pulses control current source 5.3.

A programmable current source with bipolar pulsing capabilities can support load impedances in the tens of kiloohms and currents in the tens of mA.

6. Wireless Transceiver

Any integrated circuit, discrete circuit or module that can be used to wirelessly transmit and receive information to other modules, and/or to a computer. Can be part of a network, or do point-to-point communication.

Wired communication will also be supported.

7. Power Supplies

Figure 35:
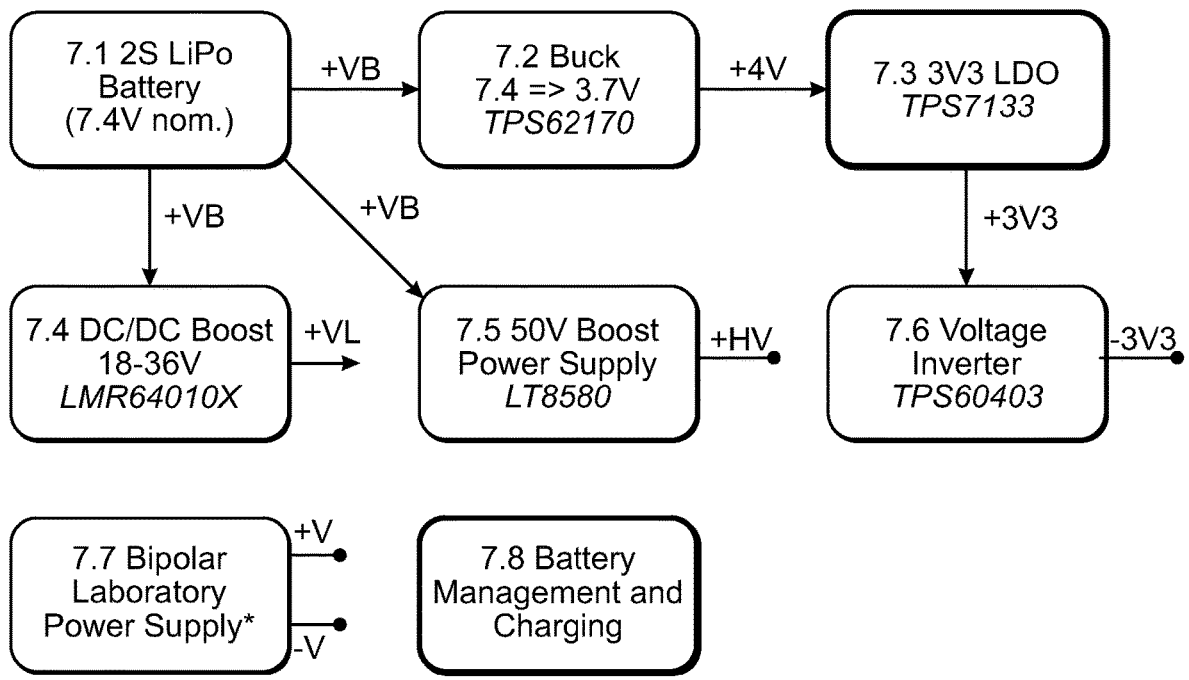
FIG. 35 is a schematic representation of power supplies suitable for use with a fifth embodiment of the invention.

With reference to FIG. 35:

7.1: Lithium-polymer battery, 2 cells in series. Can be any chemistry, any number of parallel and/or series cells. Can also be plugged in the wall.

7.2: low-voltage voltage regulator. Using a switching power supply (Buck) but could be linear, or any other topology.

7.3: linear voltage regulator.

7.4: DC/DC Boost power supply used to generate a voltage slightly above the series voltage of the LED string. Used to maximize the power efficiency of the system. Can be any topology, as long as it provides the required voltage.

7.5: DC/DC Boost power supply used to generate a high voltage for the piezo emitter. Can be any topology, as long as it provides the required voltage.

7.6: negative voltage generator (voltage inverter). Switched capacitor topology, could be anything.

7.7: lab power supply, as one suitable power supply for use with this invention.

7.8: battery charging and protection.

In one embodiment, all voltages can come from external circuits.

The full CFS architecture (FIG. 29) includes, in one embodiment, the microcontroller of FIG. 30, the electromyography unit of FIG. 31, the optical stimulation unit of FIG. 32, the sonomicrometer of FIG. 33, the functional electrical stimulation of FIG. 34 and the power supplier of FIG. 35.

All sub-modules can be on one printed-circuit board assembly (PCBA), or on multiple PCBAs, linked with wires or wirelessly. Complete modules can be networked together. Some, or all of the modules, can be implanted or external. Some, or all of the modules, can be designed in an application specific integrated circuit (ASIC). Not shown is a computer with a wireless transceiver to save, log and display data. Many modules include multiplexers. All the circuits can be multiplexed, or used as single channel units. There is no limit to the number of channels; the number 4 was selected as a compromise for early prototypes. Design can integrate an amplifier for strain gauges (direct force measurement). Design can integrate special power electronics to use piezo elements as a power source (converting muscle elongation/contraction to electricity). Design can integrate a second computing element to support more complex control loops. External sensors (e.g., switches, pressure sensors, temperature sensors, artificial finger tips, etc.) can be connected to the module and their signals can be used to control output devices.

REFERENCES

[1] Ribot-Ciscar, E., & Roll, J. P. (1998). Ago-antagonist muscle spindle inputs contribute together to joint movement coding in man. Brain Research, 791(1-2), 167-176.

[2] Kantrowitz A, Freed P S, Ciarkowski A A, et al: Development of a percutaneous energy transmission system, years 1-5 annual reports prepared for Devices and Technology Branch, Division of Heart and Vascular Diseases, Natl Heart, Lung and Blood Institute: Apr. 16, 1979, Apr. 16, 1980, Oct. 9, 1981, May 27, 1982, Jun. 5, 1983.

[3] Peckham, P. H. and J. S. Knutson, Functional electrical stimulation for neuromuscular applications. Annu Rev Biomed Eng, 2005. 7: p. 327-60.

[4] Vrbova, G., O. Hudlická, and K. S. Centofanti, Application of muscle/nerve stimulation in health and disease. Advances in muscle research. 2008, New York: Springer. xi, 118 p.

[5] Taylor, P., J. Esnouf, and J. Hobby, The functional impact of the Freehand System on tetraplegic hand function. Clinical Results. Spinal Cord, 2002. 40(11): p. 560-6.

[6] Leevering, K., P950035. Premarket Approval of Neuro-Control Corporation Freehand System. CDRH. Aug. 15, 1997.

[7] FDA File No. CardioVAD Left Ventricular Assist Device system (LVAD Technology, Inc) FDA IDE Pilot trial. 2009 G060174-5005

[8] Jackson, B. M., Gorman, J. H., Moainie, S. L., Guy, T. S., Narula, N., Narula, J., Gorman, R. C. (2002). Extension of borderzone myocardium in postinfarction dilated cardiomyopathy. Journal of the American College of Cardiology, 40(6), 1160-7; discussion 1168-71.

[9] P. H. Peckham, B. Smith, J. R. Buckett, G. B. Thrope, J. E. Letechipia, "Functional muscle stimulation system," U.S. Pat. No. 5,769,875, Jun. 23, 1998

[10] G. P. Forrest, T. C. Smith, R. J. Triolo, J. Gagnon, D. DiRisio, M. E. Miller, and L. Rhodi, "Use of the Case Western Reserve/Veterans Administration neuroprosthesis for exercise, standing and transfers by a paraplegic subject," Disability and Rehabilitation Assistive Technology, vol. 7, no. 4, pp. 340-344, 2012

[11] M. Haugland and T. Sinkjaer, "Cutaneous whole nerve recordings used for correction of foot drop in hemiplegic man," IEEE Transactions on Biomedical Engineering, vol. 3, no. 4, pp. 307-317, 1995

[12] G. S. Brindley, C. E. Polkey, D. N. Rushton, and L. Cardozo, "Sacral anterior root stimulators for bladder control in paraplegia: the first 50 cases," Journal of Neurology, Neurosurgery, & Psychiatry, vol. 49, no. 10, pp. 1104-14, 1986

[13] M. Sahin, D. M. Durand, and M. A. Haxhiu, "Chronic recordings of hypoglossal nerve activity in a dog model of upper airway obstruction," Journal of Applied Physiology, vol. 87, no. 6, pp. 2197-2206, 1999

[14] C. Veraart, M. C. Wanet-Defalque, B. Gérard, A. Vanlierde, and J. Delbeke, "Pattern recognition with the optic nerve visual prosthesis," Artificial Organs, vol. 27, no. 11, pp. 996-1004, 2003, and providing hearing ability to many otherwise deaf individuals, G. E. Loeb, "Cochlear prosthetics," Annual Review of Neuroscience, vol. 13, pp. 357-371, 1990

[15] M. G. Urbanchek, J. D. Moon, K. B. Sugg, N. B. Langhals, P. S. Cederna, Z. Baghmanli, "Regenerative peripheral nerve interface function at 1 and 3 months after implantation," Plastic & Reconstructive Surgery, vol. 130, no. 15, pp. 84, 2012.

[16] C. M. Frost, D. C. Ursu, A. Nedic, C. A. Hassett, J. D. Moon, S. L. Woo, R. B. Gillespie, P. S. Cederna, N. B. Langhals, M. G. Urbanchek, "Neuroprosthetic hand real-time proportional control by rodent regenerative peripheral nerve interfaces," Plastic & Reconstructive Surgery, vol. 133, no. 4S, pp. 1012-3, 2014.

[17] R. R. Riso, F. K. Mosallaie, W. Jensen, and T. Sinkjær, "Nerve cuff recordings of muscle afferent activity from tibial and peroneal nerves in rabbit during passive ankle motion," IEEE Transactions on Rehabilitation Engineering, vol. 8, no. 2, pp. 244-258, 2000.

[18] M. Hulliger, "The mammalian muscle spindle and its central control," Reviews of Physiology, Biochemistry and Pharmacology, vol. 101, pp. 1-110, 1984.

[19] J. A. Hoffer, A. A. Caputi, I. E. Pose, R. I. Griffiths, Prog. Brain Res. 80, 75 (1989).

[20] T. J. Roberts, R. L. Marsh, P. G. Weyand, C. R. Taylor, "Muscular force in running turkeys: the economy of minimizing work," Science, 275 (5303), 1997, 1113-1115.

[21] Markowitz, J. (2013). A Data-Driven Neuromuscular Model of Walking and its Application to Prosthesis Control by. Massachusetts Institute of Technology.

[22] Krishnaswamy, P., Brown, E. N., & Herr, H. M. (2011). Human leg model predicts ankle muscle-tendon morphology, state, roles and energetics in walking. PLoS Computational Biology, 7(3), e1001107. http://doi.org/10.1371/journal.pcbi.1001107

[23] Ortiz-Catalan, M., Brånemark, R., Håkansson, B., & Delbeke, J. (2012). On the viability of implantable electrodes for the natural control of artificial limbs: review and discussion. Biomedical Engineering Online, 11, 33. http://doi.org/10.1186/1475-925X-11-33

[24] Tan, D. W., Schiefer, M. A., Keith, M. W., Anderson, J. R., Tyler, J., & Tyler, D. J. (2014). A neural interface provides long-term stable natural touch perception. Science Translational Medicine, 6(257), 257ra138-257ra138. http://doi.org/10.1126/scitranslmed.3008669

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A closed loop system for restoring natural muscle control function to a weakened or paralyzed biological limb of a subject that suffers from impairment of a neurological control system, comprising:
   a) a sensing system including a fascicle state sensor that measures at least one member of the group consisting of a length and a velocity of a muscle in the biological limb of the subject, to generate a measured state signal of the muscle in the biological limb;
   b) a processor that processes the measured state signal to form a controlling signal; and
   c) a stimulation unit that converts the controlling signal into activation of a functionality related to that muscle in the biological limb, thereby at least partially restoring the natural muscle control function to the biological limb of the subject.

2. The system of claim 1, wherein the sensing system further includes a force sensor that measures the force of the muscle.

3. The system of claim 1, wherein the sensing system further includes an electromyographic sensor that senses an electromyographic signal of the muscle.

4. The system of claim 3, wherein the processor includes:
   a) an activation model module that processes the electromyographic signal from the muscle and thereby generates an activation signal;
   b) a neuromuscular model module that processes the measured state signal of the muscle and the activation signal to thereby estimate the force and state of the muscle; and
   c) a reflex model module that processes the estimated force and state of the muscle to thereby generate the controlling signal.

5. The system of claim 4, wherein the stimulation unit includes at least one member of the group consisting of an optogenetic stimulator and an electrical stimulator.

6. The system of claim 1, further including a percutaneous access device that enables the processor to form the controlling signal.

7. The system of claim 1, further including:
   a) an external sensing system that measures at least one of a ground reaction force, a skin strain, a pressure and a shear force; and
   b) a sensory conversion processor that converts the measurement of the external sensing system to a stimulation signal to selectively stimulate at least one afferent nerve of the subject.

8. The system of claim 1, further including a neurally-modulated reflex gain unit that carries an efferent signal from the central nervous system of the subject to the processor, whereby the controlling signal is modulated.

9. The system of claim 8, wherein the neurally-modulated reflex gain unit modulates at least one of joint torque and position of a neuromuscular model of the processor forming the controlling signal.

10. The system of claim 1, wherein the sensing system is employed to provide feedback signals to the processor to form the controlling signal to the stimulation unit that functionally stimulates muscle tissue.

11. A closed loop system for restoring lost functionality to a subject that suffers from impairment of a neurological control system, comprising:
  a) a sensing system that measures at least one member of the group consisting of a length and a velocity, to generate a measured state signal of a biological structure of the subject;
  b) a processor that processes the measured state signal to form a controlling signal;
  c) a neurally-modulated reflex gain unit that carries an efferent signal from the central nervous system of the subject to the processor, whereby the controlling signal is modulated, the neurally-modulated reflex gain unit modulating joint torque and position of a neuromuscular model of the processor forming the controlling signal; and
  d) a stimulation unit that converts the controlling signal into activation of a functionality related to that biological structure, thereby at least partially restoring the lost functionality to the subject.

* * * * *